US011685785B2

(12) United States Patent
Lu et al.

(10) Patent No.: US 11,685,785 B2
(45) Date of Patent: Jun. 27, 2023

(54) METHODS AND ANTIBODIES FOR MODULATION OF IMMUNORESPONSE

(71) Applicant: Ascendo Biotechnology, Inc., Grand Cayman (KY)

(72) Inventors: Yen-Ta Lu, Taipei (TW); Chia-Ming Chang, Taipei (TW); Tsai-Yin Wei, Changhua County (TW); I-Fang Tsai, Taipei (TW); Ling-Chiao Wu, Hsinchu (TW)

(73) Assignee: Ascendo Biotechnology, Inc., Grand Cayman (KY)

( * ) Notice: Subject to any disclaimer, the term of this patent is extended or adjusted under 35 U.S.C. 154(b) by 385 days.

(21) Appl. No.: 15/735,912

(22) PCT Filed: Jun. 12, 2016

(86) PCT No.: PCT/CN2016/085451
§ 371 (c)(1),
(2) Date: Dec. 12, 2017

(87) PCT Pub. No.: WO2016/197974
PCT Pub. Date: Dec. 15, 2016

(65) Prior Publication Data
US 2018/0362651 A1 Dec. 20, 2018

Related U.S. Application Data

(60) Provisional application No. 62/174,681, filed on Jun. 12, 2015, provisional application No. 62/174,673, filed on Jun. 12, 2015.

(51) Int. Cl.
| | | |
|---|---|---|
| *A61K 39/00* | (2006.01) | |
| *C07K 16/28* | (2006.01) | |
| *C07K 14/705* | (2006.01) | |
| *A61K 47/64* | (2017.01) | |
| *A61K 47/59* | (2017.01) | |
| *A61P 37/06* | (2006.01) | |
| *A61K 38/17* | (2006.01) | |
| *A61K 45/06* | (2006.01) | |
| *A61K 39/395* | (2006.01) | |
| *A61K 38/00* | (2006.01) | |

(52) U.S. Cl.
CPC ...... *C07K 16/2845* (2013.01); *A61K 38/1774* (2013.01); *A61K 39/3955* (2013.01); *A61K 45/06* (2013.01); *A61K 47/59* (2017.08); *A61K 47/643* (2017.08); *A61P 37/06* (2018.01); *C07K 14/705* (2013.01); *C07K 14/70503* (2013.01); *A61K 38/00* (2013.01); *C07K 2317/21* (2013.01); *C07K 2317/24* (2013.01); *C07K 2317/76* (2013.01); *C07K 2319/70* (2013.01)

(58) Field of Classification Search
CPC .............. C07K 16/2845; C07K 14/705; C07K 14/70503; C07K 2317/565; A61K 45/06; A61K 39/395; A61K 2039/505; A61P 35/00
See application file for complete search history.

(56) References Cited

U.S. PATENT DOCUMENTS

| | | |
|---|---|---|
| 8,008,449 B2 | 8/2011 | Korman et al. |
| 8,354,509 B2 | 1/2013 | Carven et al. |
| 8,900,587 B2 | 12/2014 | Carven et al. |
| 9,067,999 B1 | 6/2015 | Honjo et al. |
| 9,073,994 B2 | 7/2015 | Honjo et al. |
| 2004/0180409 A1 | 9/2004 | McVicar et al. |
| 2008/0025914 A1* | 1/2008 | Bjork, Jr. .............. A61K 51/088 424/1.53 |
| 2014/0099254 A1 | 4/2014 | Chang et al. |

FOREIGN PATENT DOCUMENTS

| | | | | |
|---|---|---|---|---|
| WO | WO-2006121168 A1 * | 11/2006 | ....... | A61K 39/39558 |
| WO | 2008/016431 A2 | 2/2008 | | |
| WO | 2008/082537 A2 | 7/2008 | | |
| WO | 2010017083 A1 | 2/2010 | | |
| WO | 2011124685 A1 | 10/2011 | | |
| WO | 2012/131004 A2 | 10/2012 | | |

OTHER PUBLICATIONS

Ohtsuji et al Arthritis Research & Therapy vol. 20 (2018) 11 pages. (Year: 2018).*
Paul, Fundamental Immunology, 3rd Edition, 1993, pp. 292-295 (Year: 1993).*
Almagro & Fransson, Frontiers in Bioscience 2008; 13:1619-33 (Year: 2008).*
Rudikoff et al(Proc. Natl. Acad. Sci. USA 1982 vol. 79: p. 1979). (Year: 1979).*
Pascalis et al. (The Journal of Immunology (2002) 169, 3076-3084) (Year: 2002).*
Casset et al. (2003) BBRC 307, 198-205, (Year: 2003).*
European Extended Search Report, dated Dec. 10, 2018, pp. 1-10.
Esponda Omar et al: "Clinical studies support a role for trem-like transcript-1 during the progression of sepsis." Boletin De La Asociacion Medica De Puerto Rico, vol. 102, No. 3, Jul. 2010 (Jul. 2010), pp. 59-61.
Christopher J Pelham et al: "Triggering receptor expressed on myeloid cells receptor family modulators: a patent review", Expert Opinion on Therapeutic Patents, vol. 24, No. 12, Nov. 1, 2014 (Nov. 1. 2014), pp. 1383-1395.
Derive M et al: TREM-like transcript-1: At the frontier between haemostasis and inflammation, HEMATOL, vol. 17, No. 6, Nov. 1, 2011 (Nov. 1, 2011), pp. 435-439.

(Continued)

*Primary Examiner* — Sheela J. Huff
(74) *Attorney, Agent, or Firm* — Lee & Hayes, P.C.

(57) ABSTRACT

A method for reversing immune suppression or immune exhaustion or for treating a disease associated with immune suppression includes: administering a composition to a subject in need of such treatments, wherein the composition contains a CD11b modulator that binds specifically to CD11b on a cell to inhibit PD-L1 expression. The CD11b modulator is an antibody or an antigen-binding portion thereof, or a compound as described.

13 Claims, 16 Drawing Sheets

Specification includes a Sequence Listing.

(56) References Cited

OTHER PUBLICATIONS

European Extended Search Report, EP App. No. 16806872.4, dated Nov. 27, 2017, pp. 1-9.

A. Sharabi et al., "A peptide based on the complementarty-determining region 1 of an autoantibody ameliorates upus by up-regulating CD4+CD25+ cells and TGF-beta," iProceedings of the National Academy of Sciences of the United States of America, National Academy of Sciences, US, Jun. 6, 2006, vol. 103, No. 23, pp. 8810-8815.

Derive, Marc et al.: Soluble Trem-like Transcript-1 Regulates Leukocyte Activation and Controls Microbial Sepsis., The Journal of Immunology, vol. 188, May 2, 2012 (May 2, 2012), pp. 5585-5592.

Standiford TJ, Keshamouni VG, (2012) Breaking the tolerance for tumor: Targeting negative regulators of TLR signaling. Oncoimmunology 1: 340-345.

Han C, Jin J, Xu S, Liu H, Li N, et al. (2010) Integrin CD11b negatively regulates TLR-triggered inflammatory responses by activating Syk and promoting degradation of MyD88 and TRIF via Cbl-b. Nat Immunol 11: 734-742.

Wang L, Gordon RA, Huynh L, Su X, Park Min KH, et al. (2010) Indirect inhibition of Toll-like receptor and type I interferon responses by ITAM-coupled receptors and integrins. Immunity 32: 518-530.

Butte MJ, Keir ME, Phamduy TB, Sharpe AH, Freeman GJ (2007) Programmed death-1 ligand 1 interacts specifically with the B7-1 costimulatory molecule to inhibit T cell responses. Immunity 27:111-122.

Francisco LM, Salinas VH, Brown KE, Vanguri VK, Freeman GJ, et al. (2009) PD-L1 regulates the development, maintenance, and function of induced regulatory T cells. J Exp Med 206: 3015-3029.

\* cited by examiner

A
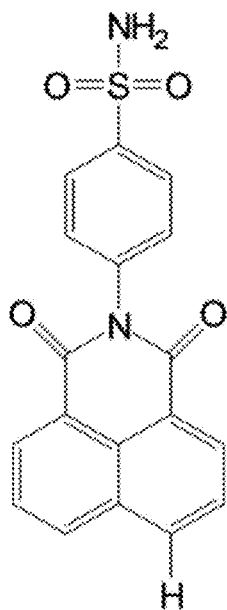
ML-C19-A
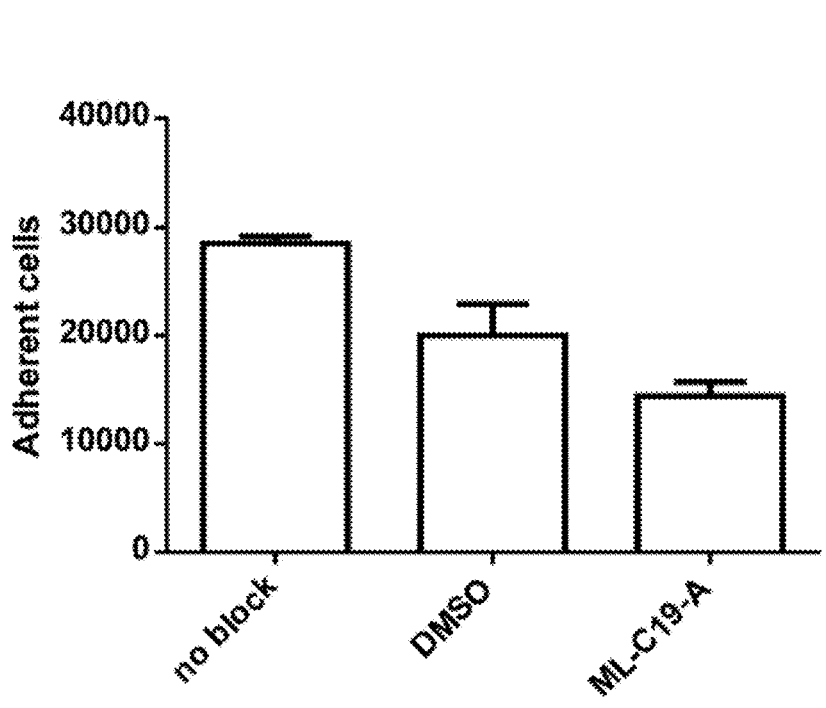
B
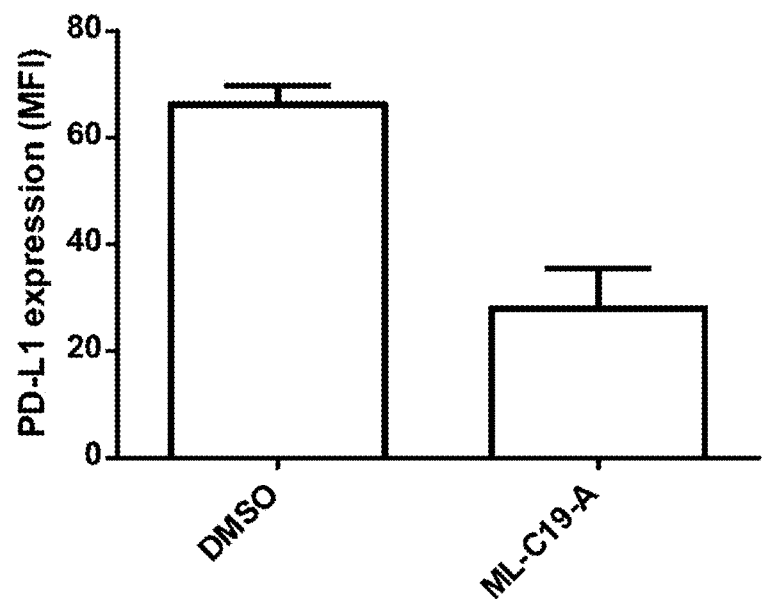
Fig. 2

```
                                CDR1                                      CDR2
VL1   1 EIVLTQSPDFQSVTPKEKVTITCRASQNIGTSIHWYQQKPDQSPKLLIKYASESISGVPS    60
VL2   1 EIVMTQSPATLSVSPGERATLSCRASQNIGTSIHWYQQKPGQAPRLLIYYASESISGIPA    60
VL3   1 DIQMTQSPSSLSASVGDRVTITCRASQNIGTSIHWYQQKPGKAPKLLIYYASESISGVPS    60
VL4   1 EIVLTQSPATLSLSPGERATLSCRASQNIGTSIHWYQQKPGQAPRLLIYYASESISGIPA    60
VL5   1 EIVLTQSPGTLSLSPGERATLSCRASQNIGTSIHWYQQKPGQAPRLLIYYASESISGIPD    60

CDR3
VL1  61 RFSGSGSGTDFTLTINSLEAEDAATYCQQSDSWPTLTFGQGTKVEIK    108
VL2  61 RFSGSGSGTEFTLTISSLQSEDFAVYYCQQSDSWPTLTFGQGTKLEIK   108
VL3  61 RFSGSGSGTDFTLTISSLQPEDFATYYCQQSDSWPTLTFGQGTKVEIK   108
VL4  61 RFSGSGSGTDFTLTISSLEPEDFAVYYCQQSDSWPTLTFGQGTKVEIK   108
VL5  61 RFSGSGSGTDFTLTISRLEPEDFAVYYCQQSDSWPTLTFGQGTKLEIK   108

CDR1                                      CDR2
LC1   1 DIVMTQSPDSLAVSLGERATINCKSSQSLLYSQNQENYLAWYQQKPGQPPKLLIYWASTR   60
LC2   1 DIVMTQSPLSLPVTPGEPASISCKSSQSLLYSQNQENYLAWYLQKPGQSPQLLIYWASTR   60
LC3   1 DIVMTQSPLSLSVTPGQPASISCKSSQSLLYSQNQENYLAWYLQKPGQSPQLLIYWASTR   60
LC4   1 DVVMTQSPLSLPVTLGQPASISCKSSQSLLYSQNQENYLAWFQQRPGQSPRRLLIYWASTR  60
LC5   1 DIVMTQTPLSLSPVTLGQPASISCKSSQSLLYSQNQENYLAWLQQRPGQPPRLLIYWASTR  60

CDR3
LC1  61 QSGVPDRFSGSGSGTDFTLTISSLQAEDVAVYYCQQYDTPLTFGQGTKVEIK   113
LC2  61 QSGVPDRFSGSGSGTDFTLKISRVEAEDVGVYYCQQYDTPLTFGQGGTKVEIK   113
LC3  61 QSGVPDRFSGSGSGTDFTLKISRVEAEDVGVYYCQQYDTPLTFGQGTKLEIK   113
LC4  61 QSGVPDRFSGSGSGTDFTLKISRVEAEDVGVYYCQQYDTPLTFGQGTKLEIK   113
LC5  61 QSGVPDRFSGSGAGTDFTLKISRVEAEDVGVYYCQQYDTPLTFGQGTKLEIK   113
```

Fig. 15

```
                          CDR1                                    CDR2
VH1   1 QVQLVQSGAEVKKPGASVKVSCKASGYTFTNYWINWVRQAPGQGLEWMGNIYPSDTYINH  60
VH2   1 QVQLVQSGAEVKKPGSSVKVSCKASGGTFSNYWINWVRQAPGQGLEWMGNIYPSDTYINH  60
VH3   1 QVQLVQSGAEVKKPGASVKVSCKASGYTFTNYWINWVRQATGQGLEWMGNIYPSDTYINH  60
VH4   1 QVQLVQSGAEVKKPGASVKVSCKASGYTFTNYWINWVRQAPGQRLEWMGNIYPSDTYINH  60
VH5   1 QVQLVQSGAEVKKPGATVKISCKVSGYTFTNYWINWVQQAPGKGLEWMGNIYPSDTYINH  60

CDR3
VH1  61 NQKFKDRVTMTRDTSTSTVYMELSSLRSEDTAVYYCARSAYANYFDYWGQGTLVTVSS  118
VH2  61 NQKFKDRVTITADKSTSTAYMELSSLRSEDTAVYYCATSAYANYFDYWGQGTLVTVSS  118
VH3  61 NQKFKDRVTMTRNTSISTAYMELSSLRSEDTAVYYCARSAYANYFDYWGQGTLVTVSS  118
VH4  61 NQKFKDRVTITRDTSASTAYMELSSLRSEDTAVYYCARSAYANYFDYWGQGTLVTVSS  118
VH5  61 NQKFKDRVTITADTSTDTAYMELSSLRSEDTAVYYCARSAYANYFDYWGQGTLVTVSR  118

CDR1                                    CDR2
HC1   1 QVQLQESGPGLVKPSETLSLTCTVSGFSLTSNSISWIRQPPGKGLEWIGAIWSGGGTDYN  60
HC2   1 QVQLQESGPGLVKPSGTLSLTCAVYGFSLTSNSISWIRQPPGKGLEWIGAIWSGGGTDYN  60
HC3   1 QVQLQQWGAGLLKPSETLSLTCAVYGESLTSNSISWIRQPPGKGLEWSAIWSGGGTDYN  60
HC4   1 EVQLVESGGGLVQPGGSLRLSCAASGFSLTSNSISWVRQAPGKGLEWVSAIWSGGGTDYN  60
HC5   1 EVQLVETGGGLIQPGGSLRLSCAASGFSLTSNSISWVRQAPGKGLEWSAIWSGGGTDYN  60

CDR3
HC1  61 SDLKSRVTISVDTSKNQFSLKLSSVTAADTAVYYCARGGYPYFDYWGQGTLVTVSS  117
HC2  61 SDLKSRVTISVDTSKNQFSLKLSSVTAADTAVYYCARGGYPYYFDYWGQGTLVTVSS  117
HC3  61 SDLKSRVTISVDTSKNQFSLKLSSVTAADTAVYYCARGGYPYYFDYWGQGTMVTVSS  117
HC4  61 SDLKSRFTISRDNSKNTLYLQMNSLRAEDTAVYYCARGGYPYYFDYWGQGTLVTVSS  117
HC5  61 SDLKSRFTISRDNSKNTLYLQMNSLRAEDTAVYYCARGGYPYYFDYWGQGTLVTVSS  117
```

Fig. 16

METHODS AND ANTIBODIES FOR MODULATION OF IMMUNORESPONSE

CROSS REFERENCE TO RELATED APPLICATIONS

This application is a U.S. National Phase Application of International Application No. PCT/CN2016/085451, filed Jun. 12, 2016, which claims priority to U.S. Provisional Application No. 62/174,681, filed Jun. 12, 2015, and U.S. Provisional Application No. 62/174,673, filed Jun. 12, 2015, all of which are hereby incorporated by reference in their entirety.

This application contains Sequence Listing, which is incorporated by reference into the specification. The Sequence Listing was filed on Dec. 12, 2017 with the application and is an ASCII text file named "BM141-US7045-Seq-List.txt" having 25 KB in size.

FIELD OF THE INVENTION

The present invention relates to the field of immunotherapy. Particularly, the present invention relates to methods and antibodies for modulating immunoresponses by regulating CD11b expression on cells.

BACKGROUND OF THE INVENTION

It is widely believed that cancer cells express immunogenic antigens can induce effective immune response against tumor formation. In additions, the tumor microenvironment is rich in components that may trigger TLR signaling to activate anti-tumor response (Standiford T J, Keshamouni V G (2012) *Breaking the tolerance for tumor: Targeting negative regulators of TLR signaling. Oncoimmunology* 1: 340-345). It means that, at initial stages of disease, cancer cells may have chance to be recognized and rejected by the immune system which exerts both host-protective- and tumor-modeling actions on developing tumors. Nonetheless, cancer cells also have numerous negative regulatory mechanisms to evade immune surveillance, such as downregulation of MHC molecules or the antigen processing and presentation machinery, increasing the secretion of inhibitory cytokines, and expressing inhibitory molecules to induce immune tolerance to cancer cells. Thus, cancer patients are often considered to have poor immunity. Thus, there is still a need to develop an agent or therapy for reversion of cancer associated immunosuppression.

Integrin alpha M (CD11b, CR3A, and ITGAM) is one protein subunit that forms the heterodimeric integrin αMβ2 molecule that expressed on the surface of many immune cells, including monocytes, granulocytes, macrophage, dendritic cells, natural killer cells, and myeloid-derived suppressor cells. Integrin αMβ2 mediates inflammation, by regulating cell adhesion, migration, chemotaxis, and phagocytosis through its promiscuous ligand repertoire. Recent research has indicated a critical role for inflammation by modulating TLR4 response (Han C, Jin J, Xu S, Liu H, Li N, et al. (2010) *Integrin CD11b negatively regulates TLR-triggered inflammatory responses by activating Syk and promoting degradation of MyD88 and TRIF via Cbl-b. Nat Immunol* 11: 734-742). A variety of endogenous integrin αMβ2 ligands within the luminal side of blood vessels, such as fibrinogen, can trigger TLR4 signaling. High avidity ligation of ITAM coupled with β2 integrin transiently induces TLR activation, but rapidly inhibits TLR signaling through targeting MyD88 and TRIF for Cbl-b-mediated proteolytic degradation. Thus integrin αMβ2 may serve as a negative regulator of that selectively inhibits components of TLR-signaling pathway to block the effects of the TLR family (Wang L, Gordon R A, Huynh L, Su X, Park Min K H, et al. (2010) *Indirect inhibition of Toll-like receptor and type I interferon responses by ITAM-coupled receptors and integrins. Immunity* 32: 518-530).

PD-L1 is one of the co-inhibitory proteins that is expressed on many types of immune cells at varying levels and is constitutively expressed on monocytes, macrophages and dendritic cells, T-cells, B-cells, epithelial cells, and vascular endothelial cells. Upon positive inductions such as IFN-γ and mitogenic stimulation, PD-L1 would be further up-regulated. PD-L1 binds to its receptor, PD-1, found on activated T cells, generating a potent immunosuppression by inducing a co-inhibitory signal in activated T-cells that promotes T-cell apoptosis and anergy (Butte M J, Keir M E, Phamduy T B, Sharpe A H, Freeman G J (2007) *Programmed death-1 ligand 1 interacts specifically with the B7-1 costimulatory molecule to inhibit T cell responses. Immunity* 27: 111-122; Francisco L M, Salinas V H, Brown K E, Vanguri V K, Freeman G J, et al. (2009) *PD-L1 regulates the development, maintenance, and function of induced regulatory T cells. J Exp Med* 206: 3015-3029). The integrity of PD-L1/PD-1 interaction is also important to avoid excessive immune responses. Defects in the interaction between PD-L1 and PD-1 may result in uncontrollable propagation of immune responses leading to conditions such as autoimmune diseases, hypersensitivity, transplantation rejection and graft versus host disorders.

U.S. Pat. No. 8,008,449 provides isolated monoclonal antibodies, particularly human monoclonal antibodies, that specifically bind to PD-1. U.S. Pat. No. 8,354,509 relates to antibodies which block the binding of human Programmed Death Receptor 1 (hPD-1) to its ligands (hPD-L1 or hPD-L2). U.S. Pat. No. 8,900,587 discloses antibodies which block binding of hPD-1 to hPD-L1 or hPD-L2 and a method of increasing the activity (or reducing downmodulation) of an immune cell through the PD-1 pathway. U.S. Pat. Nos. 9,067,999 and 9,073,994 provide compositions for cancer or infection treatment via immunopotentiation caused by inhibition of immunosuppressive signal induced by PD-1, PD-L1, or PD-L2 and therapies using them. However, the antibodies mentioned in the above patents have low response rate to therapy. US 20140099254A1 provides a method of inducing an immune response to cancer or infectious disease comprising administering to a subject with cancer or infectious disease a combination of two or more agents selected from the group consisting of (i) a leukocyte redirecting bispecific antibody including ADAM17, CD2, CD3, CD4, CD5, CD6, CD8, CD11a, CD11b, CD14, CD16, CD16b, CD25, CD28, CD30, CD32a, CD40, CD40L, CD44, CD45, CD56, CD57, CD64, CD69, CD74, CD89, CD90, CD137, CD177, CEACAM6, CEACAM8, HLA-DR alpha chain, KIR and SLC44A2; (ii) an interferon; (iii) a checkpoint inhibitor antibody including CTLA4, PD1, PD-L1, LAG3, B7-H3, B7-H4. KIR and TIM3; and (iv) an antibody-drug conjugate (ADC). However, this reference only combines a number of known immune related ingredients, while it is silent on the interplay between the ingredients.

SUMMARY OF THE INVENTION

The present invention unexpectedly found that the expression of PD-L1 can be suppressed by CD11b modulators bound to CD11b on immune cells and/or other cells. Binding of CD11b modulator to CD11b would reduce the PD-L1 expression on LPS-primed monocytes. In LPS-induced immunosuppressed monocytes or monocytes from patients with septic shock, binding of CD11b modulator to CD11b also reduces PD-L1 expression when cells are challenged with LPS.

The invention provides a method for inhibiting PD-L1 expression in an immune cell, comprising contacting the said immune cell with a CD11b modulator that binds to CD11b on the cell, hereby regulating PD-L1 expression of the immune cells.

The invention provides a method for reversing immune suppression or immune exhaustion or inducing pre-existing immunity in an immune cell, comprising contacting the said immune cell with a CD11b modulator that binds to CD11b on the cell.

The invention provides a method for determining a subject responsive to a CD11b modulator, said method comprising detecting whether PD-L1 is inhibited in a biological sample or a subject by contacting an immune cell in the biological sample or the subject with a CD11b modulator and detecting the inhibition of PD-L1 on the immune cell by the CD11b modulator, wherein the PD-L1 is inhibited indicates that the subject is responsive to a CD11b modulator.

In some embodiments, the CD11b modulator described herein is an RNAi agent inhibiting CD11b expression, an anti-CD11b antibody or a small molecular compound modulating CD11b.

In one embodiment, the immune cell is a T cell or monocyte or granulocyte or macrophage or myeloid-derived suppressor cell or natural killer cell. In one embodiment, the CD11b binding increases IFN-γ, IL-12 or CD8 T cells. In another embodiment, the binding of a CD11b modulator to CD11b on a cell treats and/or prevents a disease associated with immunosuppression. In a further embodiment, the disease associated with immunosuppression or immune exhaustion is an immune cell T-cell exhaustion in an acute and/or chronic infection, a sepsis, an immunodeficiency in cancer or an immunosenescence in aging.

In one embodiment, the method of prevention and/or treatment of a cancer comprises administering an additional active agent or therapy. In some embodiments, the additional active agent is an immune checkpoint therapy, radiotherapy or chemotherapy.

The invention also provides an anti-CD11b antibody or an antigen-binding portion thereof, comprising at least one of a heavy chain complementarity determining region 1 (H-CDR1) consisting of the amino acid residues of NYWIN (SEQ ID NO: 1) or GFSLTSNSIS (SEQ ID NO:2) or a variant having amino acid sequence with at least 85%, 90%, 91%, 92%, 93%, 94%, 95%, 96%, 97%, 98%, 99% identity to SEQ ID NO:1 or 2; a heavy chain CDR2 (H-CDR2) consisting of the amino acid residues of NIYPSDTYINHNQKFKD (SEQ ID NO:3) or AIWSGGGTDYNSDLKS (SEQ ID NO:4) or a variant having amino acid sequence with at least 85%, 90%, 91%, 92%, 93%, 94%, 95%, 96%, 97%, 98%, 99% identity to SEQ ID NO:3 or 4; and a heavy chain CDR3 (H-CDR3) consisting of the amino acid residues of SAYANYFDY (SEQ ID NO:5) or RGGYPYYFDY (SEQ ID NO:6) or a variant having amino acid sequence with at least 85%, 90%, 91%, 92%, 93%, 94%, 95%, 96%, 97%, 98%, 99% identity to SEQ ID NO:5 or 6; and at least one of a light chain CDR1 (L-CDR1) consisting of the amino acid residues of RASQNIGTSIH (SEQ ID NO:7) or KSSQSLLYSENQENYLA (SEQ ID NO:8) or a variant having amino acid sequence with at least 85%, 90%, 91%, 92%, 93%, 94%, 95%, 96%, 97%, 98%, 99% identity to SEQ ID NO:7 or 8; a light chain CDR2 (L-CDR2) consisting of the amino acid residues of YASESIS (SEQ ID NO: 9) or WASTRQS (SEQ ID NO:10) or a variant having amino acid sequence with at least 85%, 90%, 91%, 92%, 93%, 94%, 95%, 96%, 97%, 98%, 99% identity to any of SEQ ID NO:9 or 10; and a light chain CDR3 (L-CDR3) consisting of the amino acid residues QQSDSWPTLT (SEQ ID NO:11) or QQYYDTPLT (SEQ ID NO:12) or a variant having amino acid sequence with at least 85%, 90%, 91%, 92%, 93%, 94%, 95%, 96%, 97%, 98%, 99% identity to any of SEQ ID NO:11 or 12; such that said isolated antibody or antigen-binding portion thereof binds to CD11b.

In some embodiments, the CDRs described herein comprise one or more insertion, substitution and/or deletion.

In a further embodiment, the present invention provides an anti-CD11b antibody or an antigen-binding portion thereof, comprising (i) a heavy chain variable region comprising a heavy chain variable region comprising H-CDR1 comprising SEQ ID NO:1, H-CDR2 comprising SEQ ID NO:3 and H-CDR3 comprising SEQ ID NO:5, and (ii) light chain variable regions comprising L-CDR1 comprising SEQ ID NO:7, L-CDR2 comprising SEQ ID NO:9 and L-CDR3 comprising SEQ ID NO:11; or (iii) a heavy chain variable region comprising a heavy chain variable region comprising H-CDR1 comprising SEQ ID NO:2, H-CDR2 comprising SEQ ID NO:4 and H-CDR3 comprising SEQ ID NO:6, and (iv) light chain variable regions comprising L-CDR1 comprising SEQ ID NO:8, L-CDR2 comprising SEQ ID NO: 10 and L-CDR3 comprising SEQ ID NO: 12. In a further embodiment, H-CDR1 has the amino acid sequence consisting of SEQ ID NO:1 or 2; H-CDR2 has the amino acid sequence consisting of SEQ ID NO:3 or 4; H-CDR3 has the amino acid sequence consisting of SEQ ID NO:5 or 6; L-CDR1 has the amino acid sequence consisting of SEQ ID NO:7 or 8; L-CDR2 has the amino acid sequence consisting of SEQ ID NO:9 or 10 and L-CDR3 has the amino acid sequence consisting of SEQ ID NO: 11 or 12.

Further, the present invention provides a humanized anti-CD11b antibody or an antigen-binding portion thereof, comprising:

(a) a heavy chain variable region comprising an amino acid sequence consisting of SEQ ID NO: 13, and (ii) a light chain variable region comprising an amino acid sequence consisting of SEQ ID NO:23;

(c) a heavy chain variable region comprising an amino acid sequence consisting of SEQ ID NO: 14, and (ii) a light chain variable region comprising an amino acid sequence consisting of SEQ ID NO:24;

(e) a heavy chain variable region comprising an amino acid sequence consisting of SEQ ID NO: 15, and (f) a light chain variable region comprising an amino acid sequence consisting of SEQ ID NO:25;

(g) a heavy chain variable region comprising an amino acid sequence consisting of SEQ ID NO: 16, and (h) a light chain variable region comprising an amino acid sequence consisting of SEQ ID NO:26;

(i) a heavy chain variable region comprising an amino acid sequence consisting of SEQ ID NO: 17, and (j) a light chain variable region comprising an amino acid sequence consisting of SEQ ID NO:27;

(k) a heavy chain variable region comprising an amino acid sequence consisting of SEQ ID NO: 18, and (1) a light chain variable region comprising an amino acid sequence consisting of SEQ ID NO:28;

(m) a heavy chain variable region comprising an amino acid sequence consisting of SEQ ID NO: 19, and (n) a light chain variable region comprising an amino acid sequence consisting of SEQ ID NO:29;

(o) a heavy chain variable region comprising an amino acid sequence consisting of SEQ ID NO:20, and (p) a light chain variable region comprising an amino acid sequence consisting of SEQ ID NO:30;

(q) a heavy chain variable region comprising an amino acid sequence consisting of SEQ ID NO:21, and (r) a light chain variable region comprising an amino acid sequence consisting of SEQ ID NO:31; or (s) a heavy chain variable region comprising an amino acid sequence consisting of SEQ ID NO:22, and (t) a light chain variable region comprising an amino acid sequence consisting of SEQ ID NO:32.

The invention also provides compositions comprising the anti-CD11b antibody or an antigen-binding portion thereof. The invention also provides methods that comprise administering the humanized anti-CD11b antibody of the invention to a subject. Such methods include methods for inhibiting PD-L1 expression in an immune cell, reversing immune suppression or immune exhaustion or inducing pre-existing immunity in an immune cell, determining PD-L1 in a subject, and treating or preventing an acute and/or chronic infection, a in sepsis, an immunodeficiency in cancer or an immunosenescence in aging. The anti-CD11b antibodies of the invention can be used in the above-mentioned methods.

BRIEF DESCRIPTION OF THE DRAWINGS

FIGS. 2A and B show the effect of cell adhesion to fibrinogen and reduction of PD-L1 expression by binding CD11b, respectively. FIG. 2A shows the effect of ML-C19-A on K562/CD11b cell adhesion to fibrinogen. 25000 of K562/CD11b cells adhered to the bottom of fibrinogen (20 µg/ml)-coated wells in the presence of 10 µM ML-C19-A or DMSO at 37° C. for 20 min. The results were quantitated by luciferase-based CellTiter-Glo (Promega CO.). Each bar represents mean±SEM of triplicate determinations from a representative experiment. FIG. 2B shows that binding CD11b with CD11b antagonist reduces the PD-L1 expression on monocytes. Human monocytes were stimulated with LPS (100 ng/ml) in the presence of either DMSO control or 10 µM of ML-C19-A for 18 hr. The cells were harvested and PD-L1 molecules were analyzed using flow cytometry. Surface molecule expression is presented as the MFI. Values are presented as the mean±SEM from 10 independent experiments.

FIG. 15 shows the amino acid sequences of the light chain variable region of humanized CD11b antibodies. CDRs (SEQ ID NOs: 7-12) are shown in bold letters.

FIG. 16 shows the amino acid sequences of the heavy chain variable region of humanized CD11b antibodies. CDRs (SEQ ID NOs: 1-6) are shown in bold letters.

DETAILED DESCRIPTION OF THE INVENTION

Figure 1:
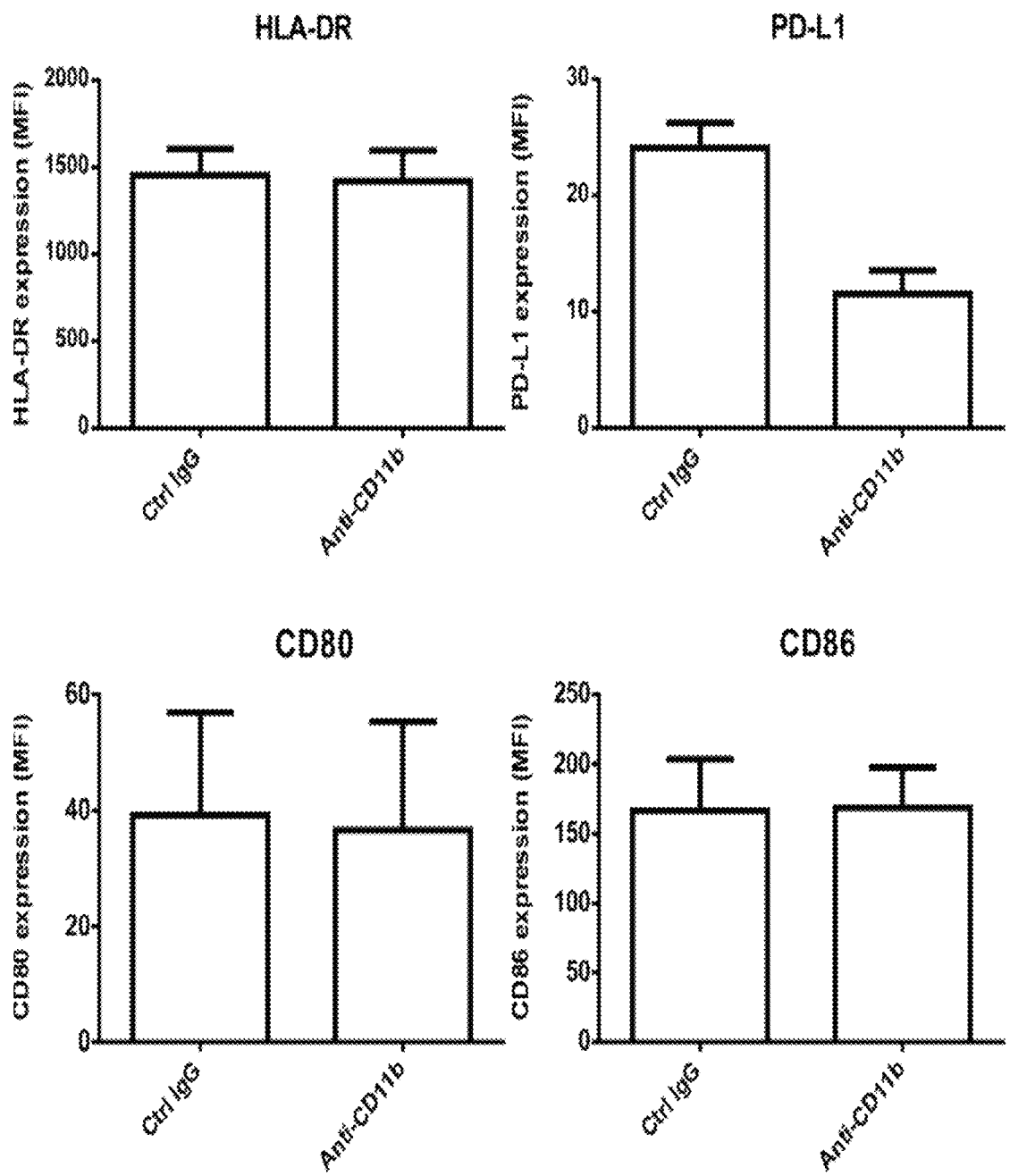
FIG. 1 shows that binding CD11b with anti-CD11b antibody alters surface expression of PD-L1. Human monocytes were stimulated with LPS (100 ng/ml) in the presence of either an isotype control IgG, or anti-CD11b antibody (ICRF44) for 18 hr. The cells were harvested and HLA-DR, PD-L1, CD80 and CD86 molecules were analyzed using flow cytometry. Surface molecule expression is presented as the MFI. Values are presented as the mean±SEM from 3 independent experiments.

Before the present composition, methods, and isolation methodologies are described, it is to be understood that this invention is not limited thereto, since such compositions, methods, and conditions may vary. It is also to be understood that the terminology used herein is for purposes of describing particular embodiments only, and is not intended to be limiting The present invention surprisingly found that the expression of PD-L1 can be suppressed by the engagement of modulators to CD11b on immune cells and/or other cells, thereby treating and/or preventing diseases associated with immunosuppression such as chronic infections, sepsis, immunodeficiency in cancer and immunosenescence in aging.

Definitions

Unless defined otherwise, all technical and scientific terms used herein have the same meaning as commonly understood by one of ordinary skill in the art to which this invention belongs. Any methods and materials similar or equivalent to those described herein can be used in the practice or testing of the invention, as it will be understood that modifications and variations are encompassed within the spirit and scope of the instant disclosure.

Unless otherwise specified, "a" or "an" means one or more.

As used herein, the amino acid residues are abbreviated as follows: alanine (Ala; A), asparagine (Asn; N), aspartic acid (Asp; D), arginine (Arg; R), cysteine (Cys; C), glutamic acid (Glu; E), glutamine (Gln; Q), glycine (Gly; G), histidine (His; H), isoleucine (Ile; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

As used herein, the term "CD11b" refers to integrin alpha M (ITGAM), which is one subunit of the heterodimeric integrin αMβ2. The second subunit of integrin αMβ2 is the common integrin 32 subunit known as CD18. Integrin αMβ2 is also call macrophage-1 antigen (Mac-1) or complement receptor 3 (CR3) which is expressed on the surface of leukocytes including monocytes, granulocytes, macrophages, and nature killer cells.

As used herein, the term "PD-L1" refers to programmed death-ligand 1 (PD-L1), cluster of differentiation 274 (CD274) or B7 homolog 1 (B7-H1). PD-L1 is a 40 kDa type 1 transmembrane protein that plays a major role in suppressing the immune system during particular events such as pregnancy, autoimmune disease, cancer, sepsis, and other infectious diseases such as *Mycobacterium tuberculosis*, cytomegalovirus, and hepatitis.

As used herein, the term "monocyte," also called mononuclear white cell, belongs to a type of white blood cell involved in first-line defensive mechanism and is recognized as able to differentiate into a dendritic cell or macrophage precursor. Monocytes normally move in the blood system. In response to external stimulating signals, monocytes secrete many immuno-regulatory cytokines, move to the site of infection in the tissues and differentiate into macrophages.

As used herein, the term "modulating" includes "increasing" or "stimulating," as well as "decreasing" or "reducing," typically in a statistically significant or a physiologically significant amount as compared to a control.

As used herein, the term "subject means a human or non-human animal selected for treatment or therapy.

As used herein, "identity" refers to a relationship between two or more polypeptide or protein sequences, as determined by comparing the sequences. In the art, "identity" also refers to the degree of sequence relatedness between polypeptides or proteins, as determined by the match between strings of such sequences. "Identity" can be easily calculated by known bioinformational methods. The "percent identity" of two polynucleotide or two polypeptide sequences is determined by comparing the sequences using the GAP computer program (a part of the GCG Wisconsin Package, version 10.3 (Accelrys, San Diego, Calif.) using its default parameters.

As used herein, the terms "peptide," "polypeptide" and "protein" each refer to a molecule comprising two or more amino acid residues joined to each other by peptide bonds. These terms encompass, e.g., native and artificial proteins, protein fragments and polypeptide analogs (such as muteins, variants, and fusion proteins) of a protein sequence as well as post-translationally, or otherwise covalently or non-covalently, modified proteins. A peptide, polypeptide, or protein may be monomeric or polymeric.

As used herein, the term "affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described below.

As used herein, the term "antibody" is used in the broadest sense and specifically covers monoclonal antibodies (including full length monoclonal antibodies), polyclonal antibodies, multispecific antibodies (e.g., bispecific antibodies), monovalent antibodies, multivalent antibodies, and antibody fragments so long as they exhibit the desired biological activity (e.g., Fab and/or single-armed antibodies).

As used herein, the term "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')2; diabodies; linear antibodies; single-chain antibody molecules (e.g., scFv); and multispecific antibodies formed from antibody fragments.

As used herein, the term "antigen-binding fragment" of an antibody, refers to one or more portions of an antibody that retain the ability to specifically bind to an antigen. It has been shown that the antigen-binding function of an antibody can be performed by fragments of a full-length antibody. Examples of binding fragments encompassed within the term "antigen-binding fragment" of an antibody include (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a Fd fragment consisting of the $V_H$ and CHI domains; (iv) a Fv fragment consisting of the $V_L$ and $V_H$ domains of a single arm of an antibody, (v) a dAb fragment which consists of a $V_H$ domain; and (vi) an isolated complementarity determining region (CDR). These antibody fragments are obtained using conventional procedures, such as proteolytic fragmentation procedures, as described in J. Goding, Monoclonal Antibodies: Principles and Practice, pp 98-118 (N.Y. Academic Press 1983). The fragments are screened for utility in the same manner as are intact antibodies.

As used herein, the term "complementarity determining regions" (CDRs) refers to the regions within antibodies where these proteins complement an antigen's shape. The acronym CDR is used herein to mean "complementarity determining region."

A "variable region" of an antibody refers to the variable region of the antibody light chain or the variable region of the antibody heavy chain, either alone or in combination. The variable regions of the heavy and light chain each consist of four framework regions (FR) connected by three CDRs also known as hypervariable regions. The CDRs in each chain are held together in close proximity by the FRs and, with the CDRs from the other chain, contribute to the formation of the antigen-binding site of antibodies. Exemplary conventions that can be used to identify the boundaries of CDRs include, e.g., the Kabat definition and the Chothia definition. The Kabat definition is based on sequence variability (see Kabat et al., 1992, Sequences of Proteins of Immunological Interest, 5th ed., Public Health Service, NIH, Washington D.C.), the Chothia definition is based on the location of the structural loop regions (Chothia et al., 1989, Nature 342:877-883). Other approaches to CDR identification include the "IMGT definition" (Lefranc, M.-P. et al., 1999, Nucleic Acids Res. 27:209-212) and the "AbM definition," which is a compromise between Kabat and Chothia and is derived using Oxford Molecular's AbM antibody modeling software, or the "contact definition" of CDRs based on observed antigen contacts, set forth in MacCallum et al., 1996, J. Mol. Biol. 262:732-745. As used herein, a CDR may refer to CDRs defined by Kabat numbering system.

As used herein, the term "humanized antibody" or a "humanized antibody fragment" is a specific type of chimeric antibody which includes an immunoglobulin amino acid sequence variant, or fragment thereof, which is capable of binding to a predetermined antigen and which, comprises one or more frameworks (FRs) having substantially the amino acid sequence of a human immunoglobulin and one or more complementarity determining regions (CDRs) having substantially the amino acid sequence of a non-human immunoglobulin. This non-human amino acid sequence often referred to as an "import" sequence is typically taken from an "import" antibody domain, particularly a variable domain. In general, a humanized antibody includes at least the CDRs or hypervariable region (HVLs) of a non-human antibody, inserted between the FRs of a human heavy or light chain variable domain.

As used herein, a "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

As used herein, the term "chimeric antibody" refers to an antibody that contains one or more regions from one antibody and one or more regions from one or more other antibodies.

As used herein, the term "heavy chain" includes a full-length heavy chain and fragments thereof having sufficient variable region sequence to confer specificity to an epitope. A full-length heavy chain includes a variable region domain, $V_H$, and three constant region domains, $CH_1$, $CH_2$, and $CH_3$. The VH domain is at the amino-terminus of the polypeptide, and the $CH_3$ domain is at the carboxyl-terminus.

As used herein, the term "light chain" includes a full-length light chain and fragments thereof having sufficient variable region sequence to confer specificity to an epitope.

A full-length light chain includes a variable region domain, $V_L$, and a constant region domain. $C_L$. Like the heavy chain, the variable region domain of the light chain is at the amino-terminus of the polypeptide.

As used herein, the term "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

As used herein, the term "subject" refers to a vertebrate, preferably a mammal, more preferably a human. Mammals include, but are not limited to, humans, farm animals, sport animals, and pets.

As used herein, the term "effective amount" refers to an amount sufficient to effect beneficial or desired clinical results. An effective amount can be administered in one or more administrations. For purposes of this invention, an effective amount is an amount that is sufficient to diagnose, palliate, ameliorate, stabilize, reverse, slow or delay the progression of the disease state.

As used herein, the terms "treatment," "treating," "treat" and the like generally refer to obtaining a desired pharmacologic and/or physiologic effect. The effect may be prophylactic in terms of completely or partially preventing a disease or symptom thereof and/or may be therapeutic in terms of a partial or complete stabilization or cure for a disease and/or adverse effect attributable to the disease. "Treatment" as used herein covers any treatment of a disease in a mammal, particularly a human, and includes: (a) preventing the disease or symptom from occurring in a subject which may be predisposed to the disease or symptom but has not yet been diagnosed as having it; (b) inhibiting the disease symptom, i.e., arresting its development; or (c) relieving the disease symptom, i.e., causing regression of the disease or symptom.

The term "preventing" as used herein refers to a preventative or prophylactic measure that stops a disease state or condition from occurring in a patient or subject. Prevention can also include reducing the likelihood of a disease state or condition from occurring in a patient or subject and impeding or arresting the onset of said disease state or condition.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

The Binding of CD-11b Modulators Affects PD-L1 Expression

The present invention surprisingly found reversion of symptoms associated with immunosuppressed state involved in the sepsis, chronic infection, and cancer through treatment with a CD11b modulator reactive with CD11b molecule expressed on the surface of immune cells.

In one aspect, the invention provides a method for inhibiting PD-L1 expression in an immune cell, comprising contacting the said immune cell with a CD11b modulator that binds CD11b on the cell, hereby inhibiting PD-L1 expression of the immune cell. Alternatively, the invention provides a use of a CD11b modulator in manufacture of a preparation for inhibiting PD-L1 expression in an immune cell. The invention also provides a CD11b modulator for inhibiting PD-L1 expression in an immune cell.

In another aspect, the invention provides a method for reversing immune suppression or immune exhaustion or inducing pre-existing immunity in an immune cell, comprising contacting the said immune cells with a CD11b modulator that binds CD11b on the cells. Alternatively, the invention provides a use of a CD11b modulator in manufacture of a preparation for reversing immune suppression or immune exhaustion or inducing pre-existing immunity in an immune cell. The invention also provides a CD11b modulator for reversing immune suppression or immune exhaustion or inducing pre-existing immunity in an immune cell.

In another aspect, the invention provides a method for determining a subject responsive to a CD11b modulator, said method comprising detecting whether PD-L1 is inhibited in a biological sample or a subject by contacting an immune cell in the biological sample or the subject with a CD11b modulator and detecting the inhibition of PD-L1 on the immune cells by the CD11b modulator, wherein the PD-L1 is inhibited indicates that the subject is responsive to a CD11b modulator.

In one embodiment, the CD11b modulator described herein is an RNAi agent inhibiting CD11b expression, an anti-CD11b antibody or a small molecular compound modulating CD11b.

In some embodiments, the RNAi agent inhibiting CD11b expression is a microRNA (miRNA) or small interfering RNA (siRNA) inhibiting CD11b expression. In some embodiments, the anti-CD11b antibody is a monoclonal, chimeric, humanized, human or bispecific anti-CD11b antibody.

In some embodiments, examples of the small molecular compound modulating CD11b include, but are not limited to, the compounds described in U.S. Pat. No. 8,268,816, US 20120035154, WO002007039616, WO002006111371, WO002007054128, WO00199901258, J Immunol 2010, 184, pp. 3917-26, and Cancer Discov, 2012, 2, pp. 1091-99. Preferably, the compound is selected from the group consisting of the following.

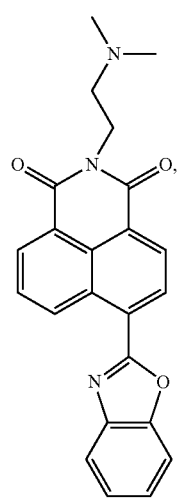

ML-A1-B

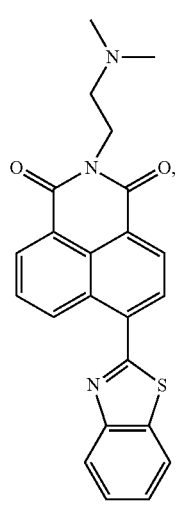
ML-A1-C
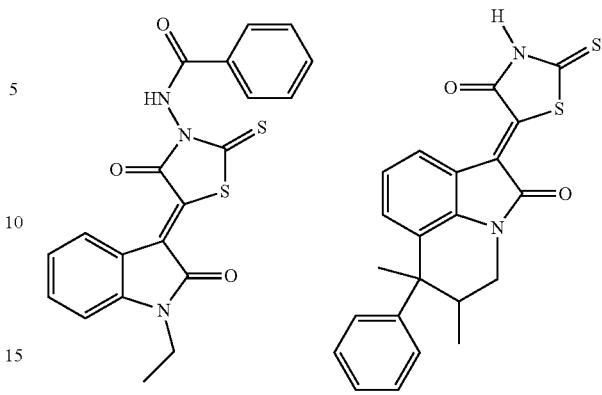
ML-C19-A
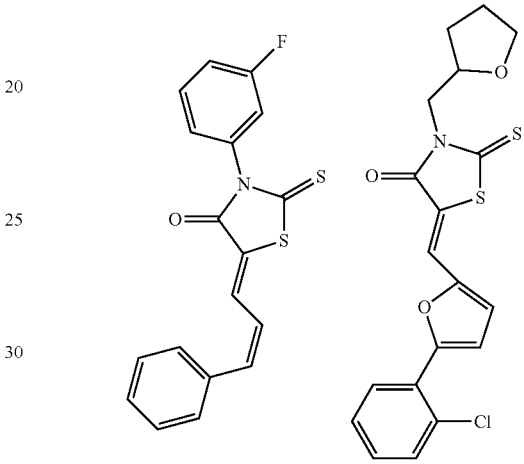
ML-C19-B
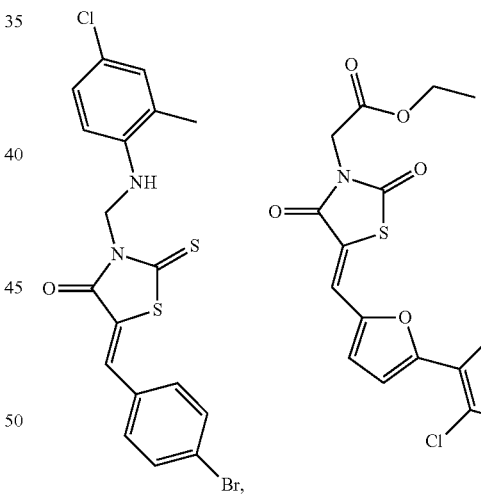
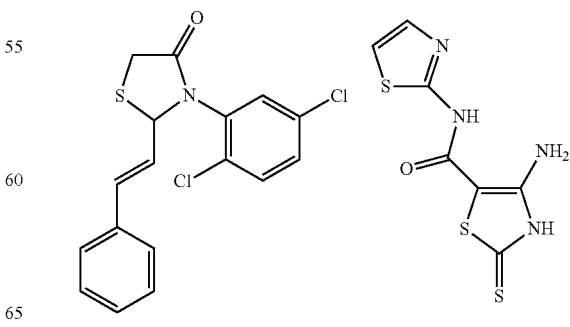

15
-continued
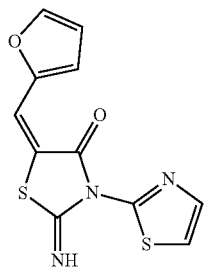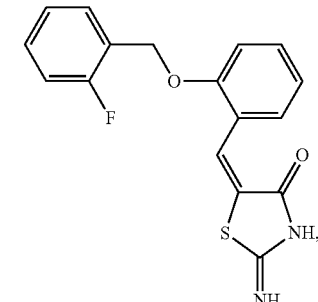
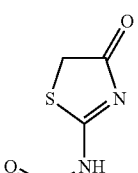
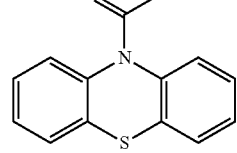
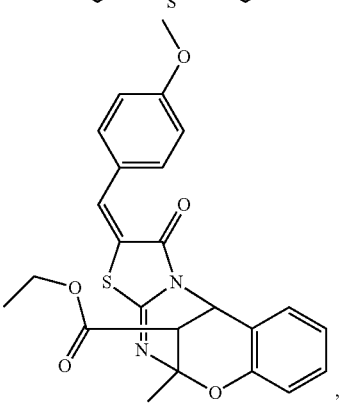
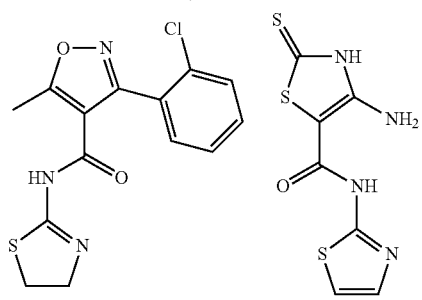
,
16
-continued
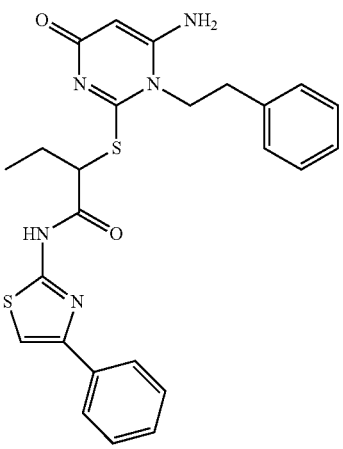
,
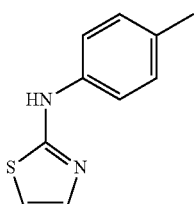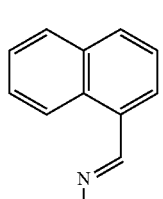
,
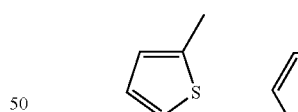
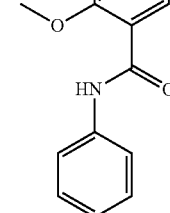

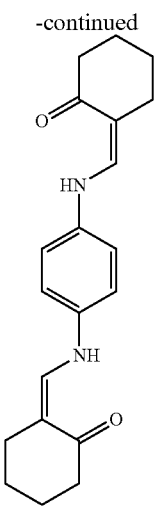

In one embodiment, the immune cell is a monocyte, granulocyte, macrophage, myeloid-derived suppressor cell or natural killer cell or T cell.

In one embodiment, the CD11b binding increases IFN-γ, IL-12 or CD8 T cells. In another embodiment, the binding of a CD11b modulator to CD11b on a cell treats and/or prevents a disease associated with immunosuppression.

In a further embodiment, the disease associated with immunosuppression or immune exhaustion is T-cell exhaustion in an acute and/or chronic infection, a sepsis, an immunodeficiency in cancer or an immunosenescence in aging. Accordingly, the invention provides a method for treating or preventing in a subject an acute and/or chronic infection, a sepsis, an immunodeficiency in cancer or an immunosenescence in aging, comprising administering an effective amount of CD11b modulator to a subject.

In one embodiment, the cancer described herein is a cancer responsive to immunotherapy. Examples of the cancer responsive to immunotherapy include, but are not limited to, melanoma, lung cancer, squamous cell carcinomas of the lung, head and neck cancer, breast cancer, ovarian cancer, uterine cancer, prostate cancer, gastric carcinoma, cervical cancer, esophageal carcinoma, bladder cancer, kidney cancer, brain cancer, liver cancer, colon cancer, bone cancer, pancreatic cancer, skin cancer, cutaneous or intraocular malignant melanoma, ovarian cancer, rectal cancer, cancer of the anal region, stomach cancer, testicular cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, esophagus cancer, small intestine cancer, endocrine system cancer, thyroid gland cancer, parathyroid gland cancer, adrenal gland cancer, sarcoma of soft tissue, urethra cancer, penis cancer, chronic or acute leukemias including acute myeloid leukemia, chronic myeloid leukemia, acute lymphoblastic leukemia, chronic lymphocytic leukemia, solid tumors of childhood, lymphocytic lymphoma, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, and T-cell lymphoma.

In one embodiment, the cancer is a cancer metastasis, refractory cancer, relapsed cancer or advanced cancer.

In one embodiment, the method of prevention and/or treatment of a cancer comprises administering an additional active agent or therapy. In some embodiments, the additional active agent is an immune checkpoint therapy, radiotherapy or chemotherapy.

In one embodiment, the CD11b modulator and the immune checkpoint therapy, radiotherapy or chemotherapy are administered simultaneously, sequentially or separately. In a further embodiment, the immune checkpoint therapy comprises administering an immune checkpoint protein. Preferably, the immune checkpoint protein is an anti-PD-1 ligand or anti-CTLA-4 antibody or anti-PD-L1 antibody, or an antigen binding fragment thereof or any combination thereof. Examples of the anti-PD-1 ligand include, but are not limited to, an anti-PD-1 antibody (such as nivolumab and pembrolizumab) and the anti-CTLA-4 antibody (such as ipilimumab).

In another embodiment, the chemotherapy comprises administering a chemotherapeutic agent. Examples of the chemotherapeutic agent include, but are not limited to, an alkylating agent, an antimetabolite, an anti-microtubule agent, a topoisomerase inhibitor or a cytotoxic antibiotic. Preferably, the chemotherapeutic agent is cisplatin, 5-Fu, taxol, docetaxel, vinorelbine, vindesine, vinflunine, gemcitabine, methotrexate, gefitinib, lapatinib or erlotinib.

The CD11b modulator and other agents described herein can be formulated as a formulation or composition. The formulations or pharmaceutical compositions of the present invention can be administered in a number of ways depending upon whether local or systemic treatment is desired and upon the area to be treated. Administration can be oral or parenteral.

In certain embodiments, the compounds and compositions as described herein are administered parenterally. Parenteral administration includes intravenous, intra-arterial, subcutaneous, intraperitoneal or intramuscular injection or infusion.

In certain embodiments, formulations or compositions for parenteral administration can include sterile aqueous solutions which can also contain buffers, diluents and other suitable additives such as, but not limited to, penetration enhancers, carrier compounds and other pharmaceutically acceptable carriers or excipients.

In certain embodiments, formulations or compositions for oral administration can include, but are not limited to, pharmaceutical carriers, excipients, powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders can be desirable.

Dosing is dependent on severity and responsiveness of the disease state to be treated, with the course of treatment lasting from several days to several months, or until a cure is effected or a diminution of the disease state is achieved. Dosing is also dependent on drug potency and metabolism.

The level of PD-L1 expression in an immune cell may serve as a new therapeutic target for reversing immunosuppression and immune exhaustion and inducing pre-existing immunity.

Anti-CD11b Antibodies of the Present Invention

Provided herein are novel anti-CD11b antibodies and methods of their use in treatment and/or prevention of diseases associated with immunosuppression and immune exhaustion, such as cancer immunotherapy, T-cell exhaustion in chronic infections, sepsis, immunodeficiency in cancer and immunosenescence in aging.

In one aspect, the present invention provides an anti-CD11b antibody or an antigen-binding portion thereof, comprising at least one of a heavy chain complementarity determining region 1 (H-CDR1) consisting of the amino acid residues of NYWIN (SEQ ID NO: 1) or GFSLTSNSIS (SEQ ID NO:2) or a variant having an amino acid sequence with at least 85%, 90%, 91%, 92%, 93%, 94%, 95%, 96%, 97%, 98%, 99% identity to SEQ ID NO:1 or 2; a heavy chain CDR2 (H-CDR2) consisting of the amino acid residues of NIYPSDTYINHNQKFKD (SEQ ID NO:3) or AIWSGGGTDYNSDLKS (SEQ ID NO:4) or a variant having an amino acid sequence with at least 85%, 90%, 91%, 92%, 93%, 94%, 95%, 96%, 97%, 98%, 99% identity to SEQ ID NO:3 or 4; and a heavy chain CDR3 (H-CDR3) consisting of the amino acid residues of SAYANYFDY (SEQ ID NO:5) or RGGYPYYFDY (SEQ ID NO:6) or a variant having an amino acid sequence with at least 85%, 90%, 91%, 92%, 93%, 94%, 95%, 96%, 97%, 98%, 99% identity to SEQ ID NO:5 or 6; and at least one of a light chain CDR1 (L-CDR1) consisting of the amino acid residues of RASQNIGTSIH (SEQ ID NO:7) or KSSQSLLY-SENQENYLA (SEQ ID NO:8) or a variant having an amino acid sequence with at least 85%, 90%, 91%, 92%, 93%, 94%, 95%, 96%, 97%, 98%, 99% identity to SEQ ID NO:7 or 8; a light chain CDR2 (L-CDR2) consisting of the amino acid residues of YASESIS (SEQ ID NO:9) or WASTRQS (SEQ ID NO:10) or a variant having an amino acid sequence with at least 85%, 90%, 91%, 92%, 93%, 94%, 95%, 96%, 97%, 98%, 99% identity to any of SEQ ID NO:9 or 10; and a light chain CDR3 (L-CDR3) consisting of the amino acid residues QQSDSWPTLT (SEQ ID NO: 11) or QQYYDTPLT (SEQ ID NO:12) or a variant having an amino acid sequence with at least 85%, 90%, 91%, 92%, 93%, 94%, 95%, 96%, 97%, 98%, 99% identity to any of SEQ ID NO:11 or 12; such that said isolated antibody or antigen-binding portion thereof binds to CD11b.

In some embodiments, the CDRs described herein comprise one or more insertion, substitution and/or deletion.

In a further embodiment, the present invention provides an anti-CD11b antibody or an antigen-binding portion thereof, comprising (i) a heavy chain variable region comprising a heavy chain variable region comprising H-CDR1 comprising SEQ ID NO:1, H-CDR2 comprising SEQ ID NO:3 and H-CDR3 comprising SEQ ID NO:5, and (ii) light chain variable regions comprising L-CDR1 comprising SEQ ID NO:7, L-CDR2 comprising SEQ ID NO:9 and L-CDR3 comprising SEQ ID NO:11; or (iii) a heavy chain variable region comprising a heavy chain variable region comprising H-CDR1 comprising SEQ ID NO:2, H-CDR2 comprising SEQ ID NO:4 and H-CDR3 comprising SEQ ID NO:6, and (iv) light chain variable regions comprising L-CDR1 comprising SEQ ID NO:8, L-CDR2 comprising SEQ ID NO: 10, and L-CDR3 comprising SEQ ID NO: 12. In a further embodiment, H-CDR1 has the amino acid sequence consisting of SEQ ID NO:1 or 2; H-CDR2 has the amino acid sequence consisting of SEQ ID NO:3 or 4; H-CDR3 has the amino acid sequence consisting of SEQ ID NO:5 or 6; L-CDR1 has the amino acid sequence consisting of SEQ ID NO:7 or 8; L-CDR2 has the amino acid sequence consisting of SEQ ID NO:9 or 10; and L-CDR3 has the amino acid sequence consisting of SEQ ID NO: 11 or 12.

In one aspect, the present invention provides a heavy chain variable region or an antigen-binding portion thereof, comprising a heavy chain variable region comprising H-CDR1 having an amino acid sequence consisting of SEQ ID NO:1 or 2, H-CDR2 having an amino acid sequence consisting of SEQ ID NO:3 or 4 and H-CDR3 having an amino acid sequence consisting of SEQ ID NO:5 or 6.

In one aspect, the present invention provides a light chain variable region or an antigen-binding portion thereof, comprising L-CDR1 having an amino acid sequence consisting of SEQ ID NO:7 or 8, L-CDR2 having an amino acid sequence consisting of SEQ ID NO:9 or 10, and L-CDR3 having an amino acid sequence consisting of SEQ ID NO:11 or 12.

In one embodiment, the present invention provides a humanized anti-CD11b antibody or an antigen-binding portion thereof, comprising (i) a heavy chain variable region comprising an amino acid sequence having at least 90%, 91%, 92%, 93%, 94%, 95%, 96%, 97%, 98%, 99% identity to any of the amino acid sequences of SEQ ID NOs:13 to 22, and (ii) a light chain variable region comprising an amino acid sequence having at least 90%, 91%, 92%, 93%, 94%, 95%, 96%, 97%, 98%, 99% identity to any of the amino acid sequences of SEQ ID NOs:23 to 32.

In a further embodiment, the present invention provides a humanized anti-CD11b antibody or an antigen-binding portion thereof, comprising a heavy chain variable region comprising an amino acid sequence consisting of SEQ ID NO: 13 to 22, and a light chain variable region comprising an amino acid sequence consisting of SEQ ID NO:23 to 32.

Preferably, the present invention provides a humanized anti-CD11b antibody or an antigen-binding portion thereof, comprising:

(a) a heavy chain variable region comprising an amino acid sequence consisting of SEQ ID NO: 13, and a light chain variable region comprising an amino acid sequence consisting of SEQ ID NO:23;

(b) a heavy chain variable region comprising an amino acid sequence consisting of SEQ ID NO: 14, and a light chain variable region comprising an amino acid sequence consisting of SEQ ID NO: 24;

(c) a heavy chain variable region comprising an amino acid sequence consisting of SEQ ID NO: 15, and a light chain variable region comprising an amino acid sequence consisting of SEQ ID NO:25;

(d) a heavy chain variable region comprising an amino acid sequence consisting of SEQ ID NO: 16, and a light chain variable region comprising an amino acid sequence consisting of SEQ ID NO: 26;

(e) a heavy chain variable region comprising an amino acid sequence consisting of SEQ ID NO: 17, and a light chain variable region comprising an amino acid sequence consisting of SEQ ID NO: 27;

(f) a heavy chain variable region comprising an amino acid sequence consisting of SEQ ID NO: 18, and a light chain variable region comprising an amino acid sequence consisting of SEQ ID NO:28;

(g) a heavy chain variable region comprising an amino acid sequence consisting of SEQ ID NO: 19, and a light chain variable region comprising an amino acid sequence consisting of SEQ ID NO:29;

(h) a heavy chain variable region comprising an amino acid sequence consisting of SEQ ID NO: 20, and a light chain variable region comprising an amino acid sequence consisting of SEQ ID NO:30;

(i) a heavy chain variable region comprising an amino acid sequence consisting of SEQ ID NO:21, and a light chain variable region comprising an amino acid sequence consisting of SEQ ID NO:31; or (j) a heavy chain variable region comprising an amino acid sequence consisting of SEQ ID NO: 22, and a light chain variable region comprising an amino acid sequence consisting of SEQ ID NO:32.

The amino acid sequences of SEQ ID NOs: 13 to 32 are listed as follows:

Heavy chain variable region of the humanized anti-CD11b antibodies of the invention:
(SEQ ID NOs: 13 to 22)

VH1
(SEQ ID NO: 13)
QVQLVQSGAEVKKPGASVKVSCKASGYTFLNYWINWVRQAPGQGLEWMGNIYPSDTYINHNQKFKDRVTMTRDTSTSTVYMELSSLRSEDTAVYYCARSAYANYFDYWGQGTLVTVSS

VH2
(SEQ ID NO: 14)
QVQLVQSGAEVKKPGSSVKVSCKASGGTFSNYWINWVRQAPGQGLEWMGNIYPSDTYINHNQKFKDRVTITADKSTSTAYMELSSLRSEDTAVYYCATSAYANYFDYWGQGTLVTVSS

VH3
(SEQ ID NO: 15)
QVQLVQSGAEVKKPGASVKVSCKASGYTFTNYWINWVRQATGQGLEWMGNIYPSDTYINHNQKFKDRVTITRDTSASTAYMELSSLRSEDTAVYYCARSAYANYFDYWGQGTLVTVSS

VH4
(SEQ ID NO: 16)
QVQLVQSGAEVKKPGASVKVSCKASGYTFTNYWINWVRQAPGQRLEWMGNIYPSDTYINHNQKFKDRVTITRDTSASTAYMELSSLRSEDTAVYYCARSAYANYFDYWGQGTLVTVSS

VH5
(SEQ ID NO: 17)
QVQLVQSGAEVKKPGATVKISCKVSGYTFTNYWINWVQQAPGKGLEWMGNIYPSDTYINHNQKFKDRVTITADTSTDTAYMELSSLRSEDTAVYYCARSAYANYFDYWGQGTLVTVSR

HC1
(SEQ ID NO: 18)
QVQLQESGPGLVKPSETLSLTCTVSGFSLTSNSISWIRQPPGKGLEWIGAIWSGGGTDYNSDLKSRVTISVDTSKNQFSLKLSSVTAADTAVYYCARRGGYPYYFDYWGQGTLVTVSS

HC2
(SEQ ID NO: 19)
QVQLQESGPGLVKPSGTLSLTCAVYGFSLTSNSISWIRQPPGKGLEWIGAIWSGGGTDYNSDLKSRVTISVDTSKNQFSLKLSSVTAADTAVYYCARRGGYPYYFDYWGQGTMVTVSS

HC3
(SEQ ID NO: 20)
QVQLQQWGAGLLKPSETLSLTCAVYGFSLTSNSISWIRQPPGKGLEWIGAIWSGGGTDYNSDLKSRVTISVDTSKNQFSLKLSSVTAADTAVYYCARRGGYPYYFDYWGQGTLVTVSS

HC4
(SEQ ID NO: 21)
EVQLVESGGGLVQPGGSLRLSCAASGFSLTSNSISWVRQAPGKGLEWVSAIWSGGGTDYNSDLKSRFTISRDNSKNTLYLQMNSLRAEDTAVYYCARRGGYPYYFDYWGQGTLVTVSS

HC5
(SEQ ID NO: 22)
EVQLVETGGGLIQPGGSLRLSCAASGFSLTSNSISWVRQAPGKGLEWVSAIWSGGGTDYNSDLKSRFTISRDNSKNTLYLQMNSLRAEDTAVYYCARRGGYPYYFDYWGQGTLVTVSS

Light chain variable region of the humanized anti-CD11b antibodies of the invention:
(SEQ ID NOs: 23 to 32)

VL1
(SEQ ID NO: 23)
EIVLTQSPDFQSVTPKEKVTITCRASQNIGTSIHWYQQKPDQSPKLLIKYASKSISGVPSRFSGSGSGTDFTLTINSLEAEDAATYYCQQSDSWPTLTFGQGTKVEIK

VL2
(SEQ ID NO: 24)
EIVMTQSPATLSVSPGERATLSCRASQNIGTSIHWYQQKPGQAPRLLIYYASESISGIPARFSGSGSGTEFTLTISSLQSEDFAVYYCQQSDSWPTLTFGQGTKLEIK

VL3
(SEQ ID NO: 25)
DIQMTQSPSSLSASVGDRVTITCRASQNIGTSIHWYQQKPGKAPKLLIYYASESISGVPSRFSGSGSGTDFTLTISSLQPEDFATYYCQQSDSWPTLTFGGGTKVEIK

VL4
(SEQ ID NO: 26)
EIVLTQSPATLSLSPGERATLSCRASQNIGTSIHWYQQKPGQAPRLLIYYASESISGIPARFSGSGSGTDFTLTISSLEPEDFAVYYCQQSDSWPTLTFGGGTKVEIK

VL5
(SEQ ID NO: 27)
EIVLTQSPGTLSLSPGERATLSCRASQNIGTSIHWYQQKPGQAPRLLIYYASESISGIPDRFSGSGSGTDFTLTISRLEPEDFAVYYCQQSDSWPTLTFGQGTKLEIK

LC1
(SEQ ID NO: 28)
DIVMTQSPDSLAVSLGERATINCKSSQSLLYSENQENYLAWYQQKPGQPPKLLIYWASTRQSGVPDRFSGSGSGTDFTLTISSLQAEDVAVYYCQQYYDTPLTFGQGTKVEIK

LC2
(SEQ ID NO: 29)
DIVMTQSPLSLPVTPGEPASISCKSSQSLLYSENQENYLAWYLQKPGQSPQLLIYWASTRQSGVPDRFSGSGSGTDFTLKISRVEAEDVGVYYCQQYYDTPLTFGGGTKVEIK

LC3
(SEQ ID NO: 30)
DIVMTQSPLSLSVTPGQPASISCKSSQSLLYSENQENYLAWYLQKPGQSPQLLIYWASTRQSGVPDRFSGSGSGTDFTLKISRVEAEDVGVYYCQQYYDTPLTFGQGTKVEIK

LC4

(SEQ ID NO: 31)
DVVMTQSPLSLPVTLGQPASISCKSSQSLLYSENQENYLAWFQQRPG

QSPRRLIYWASTRQSGVPDRFSGSGSGTDFTLKISRVEAEDVGVYYC

QQYYDTPLTFGQGTKLEIK

LC5

(SEQ ID NO: 32)
DIVMTQTPLSSPVTLGQPASISCKSSQSLLYSENQENYLAWLQQRPG

QPPRLLIYWASTRQSGVPDRFSGSGAGTDFTLKISRVEAEDVGVYYC

QQYYDTPLTFGQGTKLEIK

Techniques for preparing monoclonal antibodies against virtually any target antigen are well known in the art. See, for example, Kohler and Milstein, Nature 256: 495 (1975), and Coligan et al. (eds.), Current Protocols In Immunology, Vol. 1, pages 2.5.1-2.6.7 (John Wiley & Sons 1991). Monoclonal antibodies can be obtained by injecting mice or chicken with a composition comprising an antigen, removing the spleen to obtain B-lymphocytes, fusing the B-lymphocytes with myeloma cells to produce hybridomas, cloning the hybridomas, selecting positive clones which produce antibodies to the antigen, culturing the clones that produce antibodies to the antigen, and isolating the antibodies from the hybridoma cultures.

Various techniques, such as production of chimeric or humanized antibodies, may involve procedures of antibody cloning and construction. The antigen-binding variable light chain and variable heavy chain sequences for an antibody of interest may be obtained by a variety of molecular cloning procedures. A chimeric antibody is a recombinant protein in which the variable regions of a human antibody have been replaced by the variable regions of, for example, a mouse antibody, including the complementarity-determining regions (CDRs) of the mouse antibody. Chimeric antibodies exhibit decreased immunogenicity and increased stability when administered to a subject. Methods for constructing chimeric antibodies are well known in the art. A chimeric monoclonal antibody may be humanized by transferring the mouse CDRs from the heavy and light variable chains of the mouse immunoglobulin into the corresponding variable domains of a human antibody. The mouse framework regions (FRs) in the chimeric monoclonal antibody are also replaced with human FR sequences.

For example, a nucleic acid encoding a VL and/or VH of a humanized antibody that specifically binds CD11b can be cloned or amplified by in vitro methods, such as the polymerase chain reaction (PCR), the ligase chain reaction (LCR), the transcription-based amplification system (TAS) etc. For example, a polynucleotide encoding the protein can be isolated by polymerase chain reaction of cDNA using primers based on the DNA sequence of the molecule. A wide variety of cloning and in vitro amplification methodologies are well known to persons skilled in the art. Polynucleotides can also be isolated by screening genomic or cDNA libraries with probes selected from the sequences of the desired polynucleotide under stringent hybridization conditions.

The polynucleotides include a recombinant DNA which is incorporated into a vector; into an autonomously replicating plasmid or virus; or into the genomic DNA of a prokaryote or eukaryote, or which exists as a separate molecule (for example, a cDNA) independent of other sequences. The nucleotides of the invention can be ribonucleotides, deoxyribonucleotides, or modified forms of either nucleotide. The term includes single and double forms of DNA.

DNA sequences encoding a VL and/or VH of a humanized antibody that specifically binds CD11b can be expressed in vitro by DNA transfer into a suitable host cell. The cell may be prokaryotic or eukaryotic. The term also includes any progeny of the subject host cell. It is understood that all progeny may not be identical to the parental cell since there may be mutations that occur during replication. Methods of stable transfer, meaning that the foreign DNA is continuously maintained in the host, are known in the art.

Polynucleotide sequences encoding a VL and/or VH of a humanized antibody that specifically binds CD11b can be operatively linked to expression control sequences. An expression control sequence operatively linked to a coding sequence is ligated such that expression of the coding sequence is achieved under conditions compatible with the expression control sequences. The expression control sequences include, but are not limited to, appropriate promoters, enhancers, transcription terminators, a start codon (for instance, ATG) in front of a protein-encoding gene, splicing signal for introns, maintenance of the correct reading frame of that gene to permit proper translation of mRNA, and stop codons.

The polynucleotide sequences encoding a VL and/or VH of a humanized antibody that specifically binds CD11b can be inserted into an expression vector. Examples of the expression vector include, but are not limited to, a plasmid, virus or other vehicle that can be manipulated to allow insertion or incorporation of sequences and can be expressed in either prokaryotes or eukaryotes. Hosts can include microbial, yeast, insect and mammalian organisms. Methods of expressing DNA sequences having eukaryotic or viral sequences in prokaryotes are well known in the art. Biologically functional viral and plasmid DNA vectors capable of expression and replication in a host are known in the art. Transformation of a host cell with recombinant DNA may be carried out by conventional techniques well known to those skilled in the art.

Isolation and purification of recombinantly expressed polypeptides may be carried out by conventional means including preparative chromatography and immunological separations.

Humanization can be performed generally following conventional methods known in the art, by substituting rodent CDRs or CDR sequences for the corresponding sequences of a human antibody. Accordingly, such "humanized" antibodies are antibodies wherein substantially less than an intact human variable domain has been substituted by the corresponding sequence from a non-human species. In practice, humanized antibodies are typically human antibodies in which some CDR residues and possibly some FR residues are substituted by residues from analogous sites in non-human, for example, rodent antibodies.

The choice of human variable domains, both light and heavy, to be used in making the humanized antibodies is very important to reduce antigenicity. The sequence of the variable domain of a rodent antibody is screened against the entire library of known human variable-domain sequences. The human sequence which is closest to that of the rodent is then accepted as the human framework (FR) for the humanized antibody. Another method uses a particular framework derived from the consensus sequence of all human antibodies of a particular subgroup of light or heavy chains. The same framework may be used for several different humanized antibodies.

Antibody binding portions include, for example, Fab, Fab', F(ab)$_2$, F(ab')$_2$, Fv, scFv and the like. These fragments are produced from intact antibodies using methods well known in the art, for example by proteolytic cleavage with enzymes such as papain (to produce Fab fragments) or pepsin (to produce F(ab')$_2$ fragments).

Modifications can be made to a nucleic acid encoding a polypeptide described herein without diminishing its biological activity. Some modifications can be made to facilitate the cloning, expression, or incorporation of the targeting molecule into a fusion protein. Such modifications are well known to those of skill in the art and include, for example, termination codons, a methionine added at the amino terminus to provide an initiation, site, additional amino acids placed on either terminus to create conveniently located restriction sites, or additional amino acids to aid in purification steps. In addition to recombinant methods, the antibodies of the present disclosure can also be constructed in whole or in part using standard peptide synthesis well known in the art.

In another aspect, the present invention provides compositions comprising an anti-CD11b antibody of the invention. In some embodiments, such compositions may be administered to subjects. In some embodiments, the anti-CD11b antibody of the invention may be provided in a composition that comprises one or more other components, including, but not limited to, pharmaceutically acceptable carriers, adjuvants, wetting or emulsifying agents, pH buffering agents, preservatives, and/or any other components suitable for the intended use of the compositions. Such compositions can take the form of solutions, suspensions, emulsions and the like. The term "pharmaceutically acceptable carrier" includes various diluents, excipients and/or vehicles. The pharmaceutically acceptable carrier includes, but is not limited to, carriers known to be safe for delivery to human and/or other animal subjects, and/or approved by a regulatory agency of the federal or a state government, and/or listed in the U.S. Pharmacopeia, and/or other generally recognized pharmacopeia, and/or receiving specific or individual approval from one or more generally recognized regulatory agencies for use in humans and/or other animals. Such pharmaceutically acceptable carriers, include, but are not limited to, water, aqueous solutions (such as saline solutions, buffers, and the like), organic solvents (such as certain alcohols and oils, including those of petroleum, animal, vegetable or synthetic origin, such as peanut oil, soybean oil, mineral oil, sesame oil) and the like.

In one embodiment, the humanized anti-CD11b antibody of the invention may be provided in a composition that comprises one or more "chemotherapeutic agents" that are chemical compounds used in the treatment of a cancer, also called anti-neoplastic drugs. An anti-nucleoplastic drug is usually classified, according to differences in the chemical structure and origin of the drug, into alkylating agents, anti-metabolic drugs, anti-neoplastic antibiotics, anthracycline antibiotics, anti-neoplastic herbal drugs, and hormones. Depending on the cycle or phase specificity, the chemotherapeutic drugs against tumor can be classified into (1) cell cycle non-specific agents (CCNSA), such as alkylating agents, anti-neoplastic antibiotics and platinum coordination complexes, etc., and (2) cell cycle specific agents (CCSA), such as anti-metabolic drugs, vinca alkaloids, etc.

In some embodiments, the compositions of the invention comprise an "effective amount" of an anti-CD11b antibody of the invention. An "effective amount" is an amount required to achieve a desired end result. The amount of a humanized anti-CD11b antibody of the invention that is effective to achieve the desired end result will depend on a variety of factors including, but not limited to, the species of the intended subject (e.g. whether human or some other animal species), the age and/or sex of the intended subject, the planned route of administration, the planned dosing regimen, the seriousness of any ongoing diseases or conditions, and the like. The effective amount—which may be a range of effective amounts—can be determined by standard techniques without any undue experimentation, for example using in vitro assays and/or in vivo assays in the intended subject species or any suitable animal model species. Suitable assays include, but are not limited to, those that involve extrapolation from dose-response curves and/or other data derived from in vitro and/or in vivo model systems. In some embodiments the effective amount may be determined according to the judgment of a medical or veterinary practitioner based on the specific circumstances.

In one embodiment, an effective amount of the humanized anti-CD11b antibody ranges from about 0.01 mg/kg to about 40 mg/kg of body weight per administration; preferably, about 0.01 mg/kg to about 30 mg/kg, about 0.01 mg/kg to about 20 mg/kg, about 0.01 mg/kg to about 10 mg/kg, about 1 mg/kg to about 40 mg/kg, about 1 mg/kg to about 30 mg/kg, about 1 mg/kg to about 20 mg/kg, about 1 mg/kg to about 10 mg/kg, about 2 mg/kg to about 40 mg/kg, about 2 mg/kg to about 30 mg/kg, about 2 mg/kg to about 20 mg/kg, about 2 mg/kg to about 10 mg/kg, about 5 mg/kg to about 40 mg/kg, about 5 mg/kg to about 30 mg/kg, about 5 mg/kg to about 20 mg/kg or about 5 mg/kg to about 10 mg/kg or about 1 mg/kg to about 5 mg/kg.

In some embodiments, the present invention provides methods that comprise administering the humanized anti-CD11b antibody of the invention to a subject. Such methods include methods for inhibiting PD-L1 expression in an immune cell, reversing immune suppression or immune exhaustion or inducing pre-existing immunity in an immune cell, detecting PD-L1 in a subject, and treating or preventing an acute and/or chronic infection, a sepsis, an immunodeficiency in cancer or an immunosenescence in aging. The anti-CD11b antibodies of the invention can be used in the above-mentioned methods.

The cancer described herein is a cancer responsive to immunotherapy and the examples of the cancers are as described herein. The method of prevention and/or treatment of a cancer comprises administering an additional active agent or therapy. The additional active agents, their embodiments and administrations are as described herein.

Subjects to which the anti-CD11b antibody of the invention, or compositions comprising the anti-CD11b antibody, can be administered (for example in the course of a method of treatment) include any and all animal species. In some embodiments, the subjects are mammalian species. Mammalian subjects include, but are not limited to, humans, non-human primates, rodents, rabbits, and ferrets.

Various delivery systems are known in the art and any suitable delivery system can be used to administer the compositions of the present invention to subjects. Such delivery systems include, but are not limited to, intradermal, intramuscular, intraperitoneal, intravenous, subcutaneous, intranasal, epidural, and oral delivery systems. The compositions of the present invention may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

In some such embodiments, administration of a single dose is preferred. However, in other embodiments, additional dosages can be administered, by the same or different route to achieve the desired effect. In some embodiments, dosing regimens may comprise a single administration. In other embodiments, dosing regimens may comprise multiple administrations.

EXAMPLES

The materials and methods used in the following examples are described below.

Materials and Methods

Human Cell Isolation and Cell Culture

White blood cell concentrates from healthy volunteers were obtained from the Taiwan Blood Service Foundation (Taipei, Taiwan). Written informed consent was obtained for participation in the study, which was approved by the Institutional Review Board of the Mackay Memorial Hospital. Human monocytes were isolated as previous described. In brief, peripheral blood mononuclear cells (PBMCs) were isolated using Ficoll-Paque Plus (GE Healthcare) gradient centrifugation. The monocytes were further purified by conducting CD14 selection using CD14 MACS microbeads (Miltenyi Biotec). The purity of monocytes confirmed using flow cytometry analysis was approximately 90%.

Animal and Tumor Cell Line.

C57BL/6 mice (6 to 8 weeks old) were purchased from the National Laboratory Animal Center (Taipei, Taiwan). All animal experiments were performed under specific pathogen-free conditions and in accordance with guidelines approved by the Animal Care and Usage Committee of Mackay memorial hospital (Taipei, Taiwan). The body weight of each mouse was measured at the beginning of treatment and every day during the treatment period. B16F10 are murine melanoma cells and LLC1 are murine Lewis lung carcinoma. All cells were derived from C57BL/6 mice. Cells were maintained in Dulbecco's modified Eagle's medium (DMEM), 10% heat-inactivated fetal calf serum, 2 mM L-glutamine, penicillin (100 U/ml), and streptomycin (100 µg/ml) at 37 C in a 5% $CO_2$ humidified atmosphere.

Antibodies and Reagents

For Human Monocytes Study

LPS from *E. coli* (O111:B4) was obtained from Sigma. Murine binding antibodies specific to human CD11b (ICRF44) and mouse IgG1 used for a control antibody were purchased from Biolegend.

For Murine Cancer Model

Rat binding antibody specific to murine CD11b (M1/70), rat control IgG2b antibody (LTF-2), Armenian hamster anti-murine PD1 (J43), and Armenian hamster control IgG were purchased from BioXcell. Taxol is a chemotherapy drug obtained from MacKay Memorial hospital Protocol of Cancer Treatment Subcutaneous Tumor Model C57BL/6 mice were inoculated subcutaneously with $2\times10^5$ B16F10 cells or $1\times10^6$ LLC1 cells. 7 days after tumor inoculation, treatment was started. Tumor-bearing mice were treated intraperitoneally (ip) with different antibodies and a chemotherapy drug twice per week. Mice were monitored and scored for the formation of palpable tumors twice weekly and sacrificed if tumors exceeded the predetermined size of 3000 $mm^3$. Tumor volumes were measured with calipers and calculated with the following formula: $A \times B^2 \times 0.54$, where A is the largest diameter, and B is the smallest diameter.

Lung Metastasis Model $2\times10^5$ B16F10 cells or LLC1 cells were injected into each mouse via tail vein on day 0. On day1, mice were injected ip with various antibodies. Injections were repeated every three to four days. On day15, mice were sacrificed and the amount of tumor seeding was counted as total numbers of nodules presented in the lungs under microscopy. In other experiments, mice were analyzed for the effects of combination therapy for the long term survival of treated mice in each of the groups.

Flow Cytometric Analysis

For Human Monocyte Study

Monocytes were pre-incubated anti-CD11b (ICRF44), or appropriate isotype control antibodies for 1 hour. The cells were subsequently added with 100 ng/ml LPS and incubated overnight. To analyze the surface phenotype of the LPS primed monocytes, the cells were incubated for 30 minutes on ice in the dark with the following mAbs diluted in phosphate-buffered saline (PBS) containing 1% BSA: PD-L1-FITC, CD80-PE, CD86-PE, HLA-DR-PE, and CD14-PerCP (BD Biosciences). Monocytes, polymorphonuclear leukocytes (PMNs), and lymphocytes are gated based on their FSC/SSC properties. The fluorescence was detected using FACS Calibur, and data analysis was performed using FCS Express version 3 (De Novo Software).

For Murine Cancer Study

To obtain tumor-infiltrating leukocytes, tumor tissues were digested by collagenase IV (Sigma). Single-cell suspensions were stained with following antibodies: CD45-PE, Ly-6G-FITC, Ly-6C-APC, and CD8b.2-FITC. Tumor-infiltrating leukocytes were gated from CD45+ populations. The fluorescence was detected using FACS Calibur, and data analysis was performed using FCS Express version 3 (De Novo Software).

To isolate white blood cells (WBCs) from each experiment, whole blood cells were lysed by RBC lysis buffer. Single-cell suspensions were stained with following antibodies: PD-L1-APC, IAIE-APC, and CD8b.2-FITC (Biolegend). Monocytes, polymorphonuclear leukocytes (PMNs), and lymphocytes were based on their FSC/SSC properties. The fluorescence was detected using FACS Calibur, and data analysis was performed using FCS Express version 3 (De Novo Software).

Cytokine Quantification

Human IL-6, IL-10, IL-12, and TNF-α in the culture supernatant were detected by a commercial enzyme-linked immunosorbent assay (ELISA; R&D Systems) according to the manufacturer instructions. Murine IL-12, IFN-γ, and TNF-α in the plasma were quantified by BD CBA mouse inflammation kit.

Example 1 Binding CD11b would Reduce the PD-L1 Expression on LPS-Primed Monocytes In this example, we investigated whether blockade of the integrin αMβ2 (Mac-1), could functionally increase the TLR response. As shown in FIG. 1, administration of CD11b binding agent such as anti-CD11b antibody (ICRF44) can reduce the LPS induced PD-L1 expression on monocytes. By contrast, anti-CD11b antibody treatment did not alter the levels of HLA-DR, CD80, and CD86 expression on LPS-primed monocytes. Binding CD11b with ML-C19-A, a small molecule of CD11b antagonist (FIG. 2A), also demonstrated inhibitory PD-L1 expression in LPS-primed monocytes (FIG. 2B). Together, these results suggest that CD11b plays a crucial role in the induction of PD-L1 expression on LPS-primed monocytes.

Example 2 Effect of CD11b Binding in Antitumor Immunity

Figure 3:
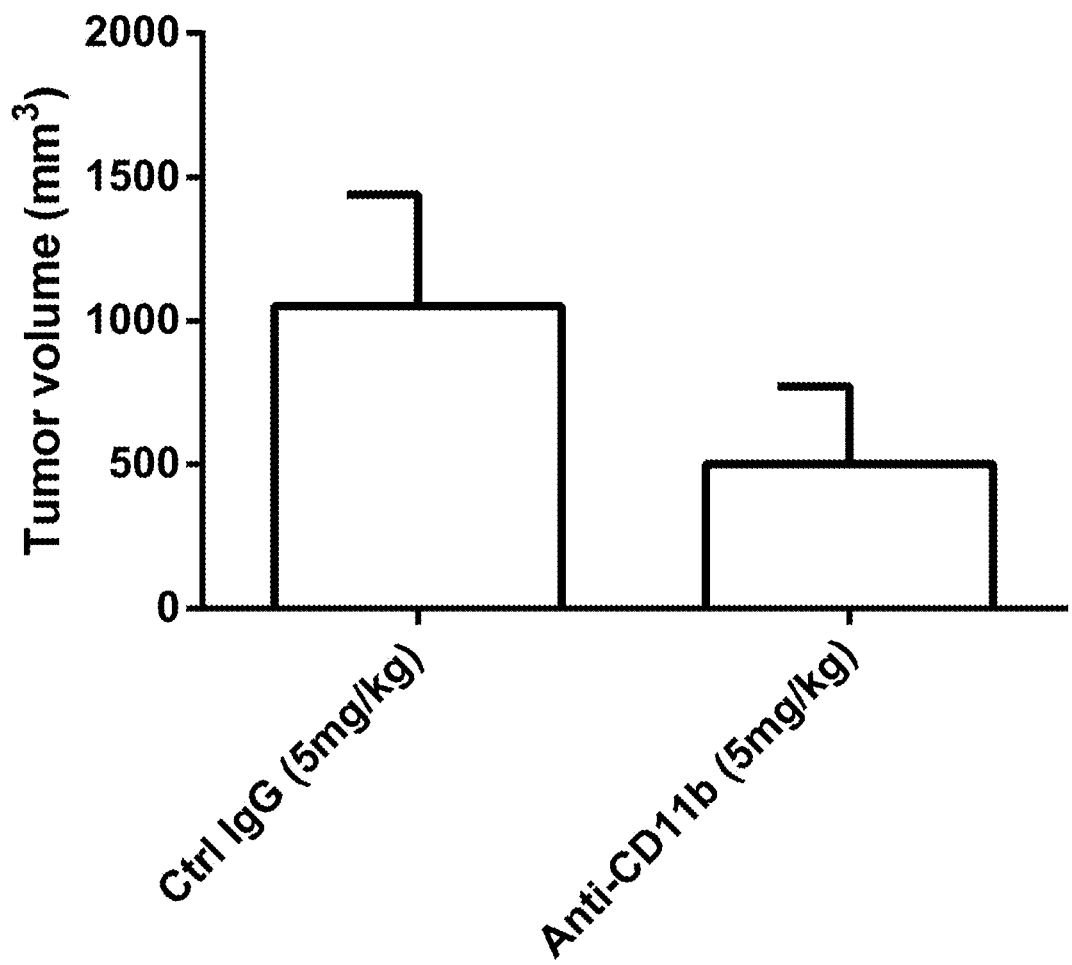
FIG. 3 shows the effect of anti-CD11b antibody monotherapy on the growth of B16F10 tumor. C57BL/6 mice were subcutaneously injected with $2\times10^5$ B16F10 cells at Day 0. On day 7, mice (n=5/group) were injected ip with either control IgG (5 mg/kg) or Rat anti-mouse CD11b antibody. Injections were repeated every three to four days. On Day 18, mice were sacrificed. Tumor volumes and were measured and the results are presented as the mean±SEM.
Figure 4:
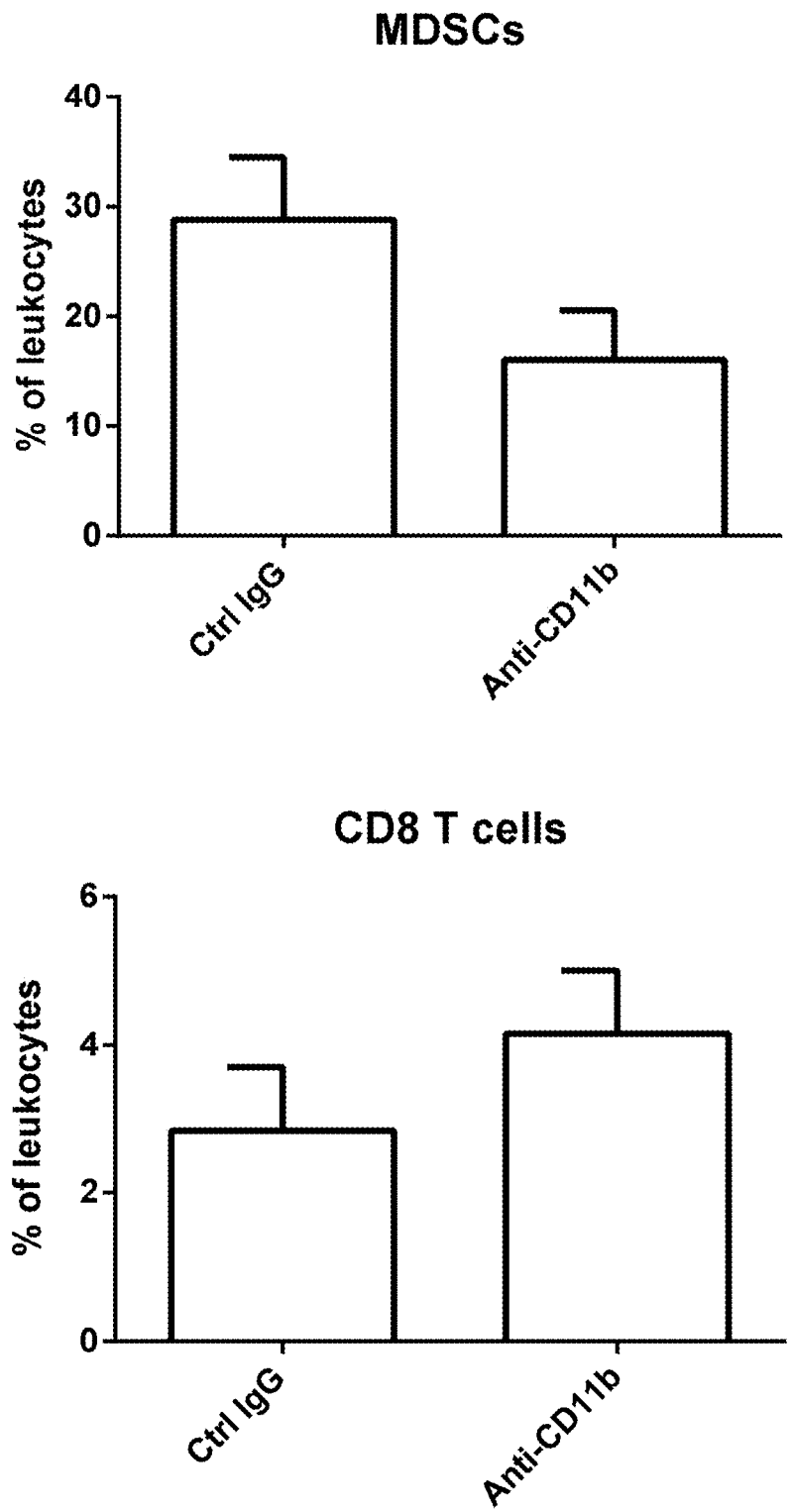
FIG. 4 shows MDSCs and CD8 T cells population in tumor-infiltrating leukocytes after anti-CD11b antibody treatment. C57BL/6 mice were subcutaneously injected with $2\times10^5$ B16F10 cells at Day 0. On day 7, mice (n=5/group) were injected ip with either control IgG (5 mg/kg) or Rat anti-mouse CD11b antibody. Injections were repeated every three to four days. On Day 18, mice were sacrificed. Tumors were digested with collagenase and tumor-infiltrating leukocytes were analyzed by flow cytometry.
Figure 5:
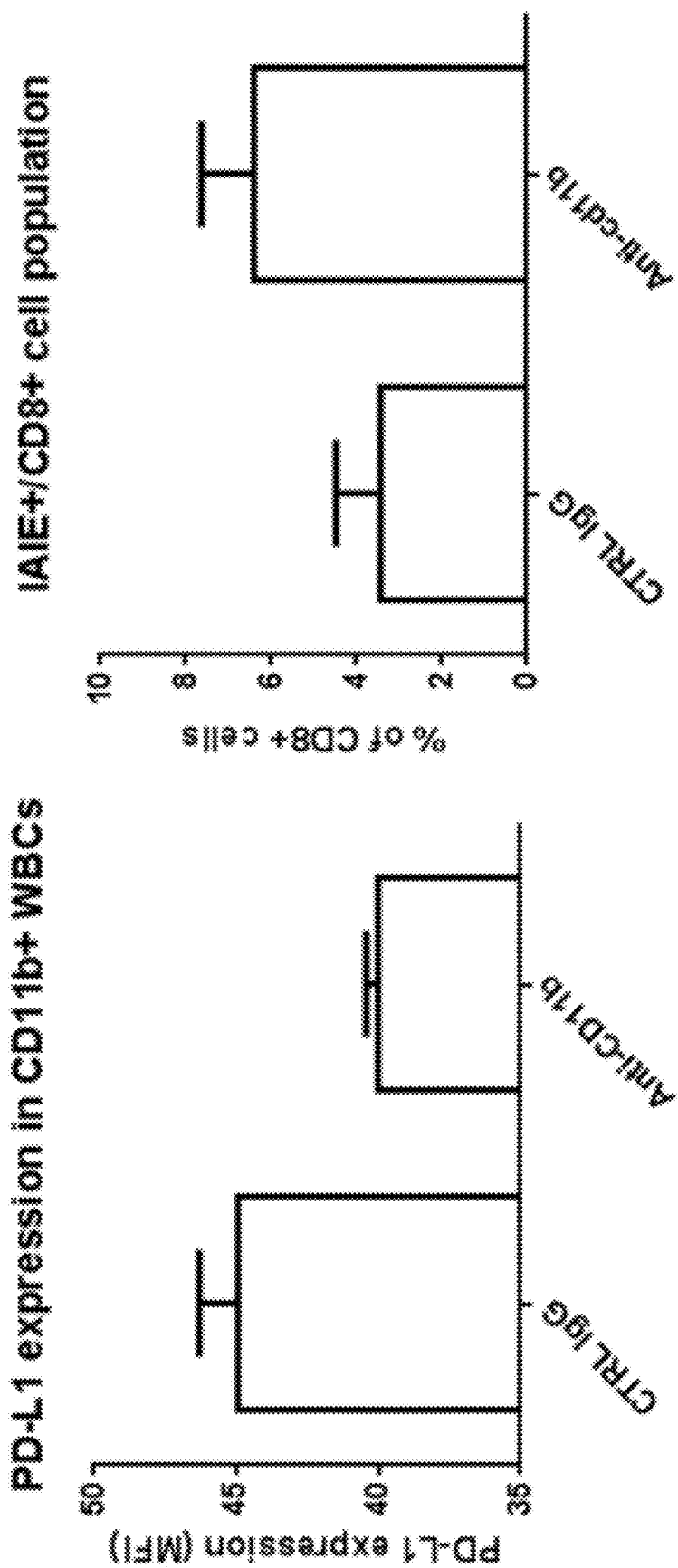
FIG. 5 shows PD-L1 expressions on WBCs and IAIE+/CD8 T cells in the blood after anti-CD11b treatment. $2\times10^5$ B16F10 cells were injected into each mouse via tail vein on day 0. On day 1, mice (n=3/group) were injected ip with either control IgG (5 mg/kg), or anti-mouse CD11b antibody (5 mg/kg). Injections were repeated every three to four days. On day15, mice were sacrificed. The WBCs cells were harvested and PD-L1 molecules and IAIE+/CD8 T cells were analyzed using flow cytometry.
Figure 6:
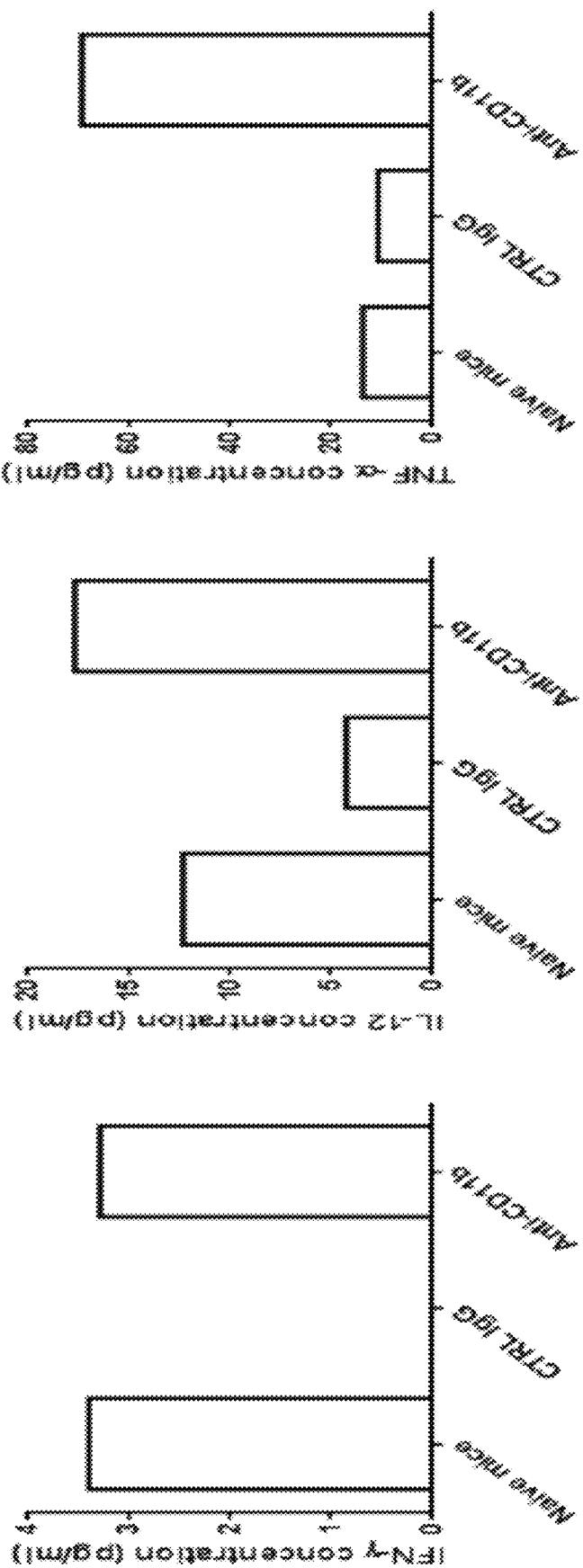
FIG. 6 shows that production of IFN-γ, IL-12 and TNF-α in tumor-bearing mice is reversed by treatment with anti-CD11b antibody. $2\times10^5$ B16F10 cells were injected into each mouse via tail vein on day 0. On day1, mice (n=3/group) were injected ip with either control IgG (5 mg/kg) or Rat anti-mouse CD11b antibody (5 mg/kg). Injections were repeated every three to four days. On day 9, mice were sacrificed. Plasma cytokines were quantified by BD CBA mouse inflammation kit.

To examine the effect of CD11b binding in antitumor immunity, anti-mouse CD11b (M1/70) antibody was tested as a monotherapy in B16F10 murine tumor model. C57BL/6 mice were subcutaneously injected with B16F10 cells at Day 0. On day 7, mice were injected intraperitoneally (ip) with either control IgG (5 mg/kg) or anti-mouse CD11b antibody (5 mg/kg). Injections were repeated every three to four days. Efficiency was determined by monitoring tumor volumes and long term survival for each group. As shown in FIG. 3, binding CD11b with anti-mouse CD11b antibody potently inhibited the subcutaneous growth of B16F10 tumors (control IgG vs. anti-CD11b=1054±385.4 mm$^3$ vs. 502.7±268.2 mm$^3$ on day 18). We examined the proportion of immune cell populations in the tumor. On day 18 after tumor inoculation, binding CD11b with anti-CD11b antibody reduced the local accumulation of tumor-infiltrating myeloid-derived suppressor cells (MDSCs), which suppress T cells and resulted in an increase in tumor infiltrated CD8 T cells (FIG. 4). Together, binding CD11b with anti-CD11b antibody shifted an immunosuppressive tumor microenvironment to an immunostimulatory state, which favorably contributes to an antitumor effect. We further examined the proportion of immune cell populations in the periphery after anti-CD11b antibody treatment. On day 15 after tumor injection, anti-CD11b treatment resulted in a decrease PD-L1 expression in CD11b positive white blood cells, while the percentages of IAIE positive CD8 T cells, activated T cells, in CD8 T cells were increased (FIG. 5). Plasma levels of IFN-γ, IL-12, and TNF-α reflect immunostimulatory state in various inflammatory or malignant diseases. We measured plasma IFN-γ, IL-12, and TNF-α levels in tumor-bearing mice with anti-CD11b antibody treatment. In comparison to control IgG treatment, anti-CD11b antibody treated mice showed elevated plasma IFN-γ, IL-12, and TNF-α levels (FIG. 6).

Figure 7:
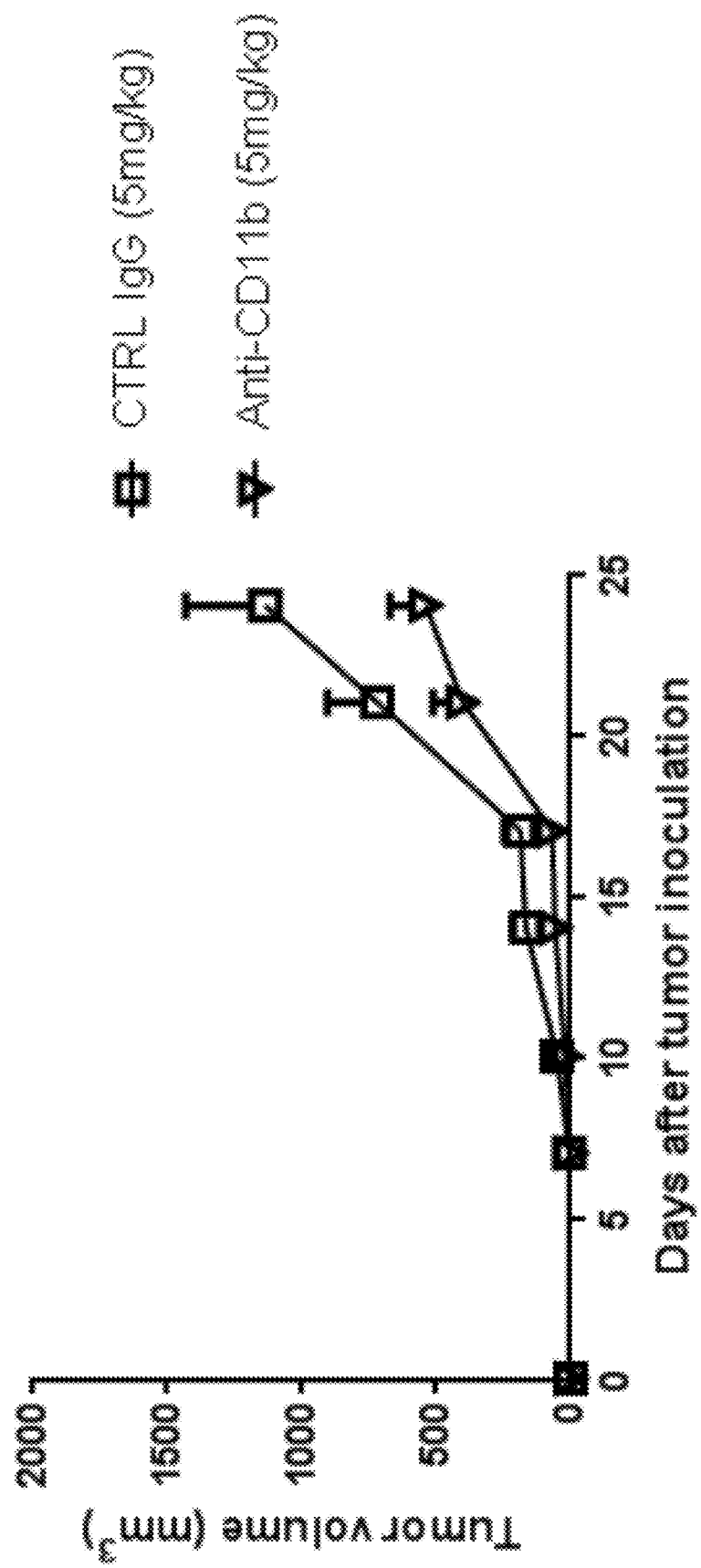
FIG. 7 shows the effect of anti-CD11b antibody monotherapy on the growth of LLC1 tumor. C57BL/6 mice were subcutaneously injected with $1\times10^6$ LLC1 cells at Day 0. On day 7, mice (n=5/group) were injected ip with either control IgG (5 mg/kg) or Rat anti-mouse CD11b antibody. Injections were repeated every three to four days. Tumor volumes were measured and the results are presented as the mean±SEM.
Figure 8:
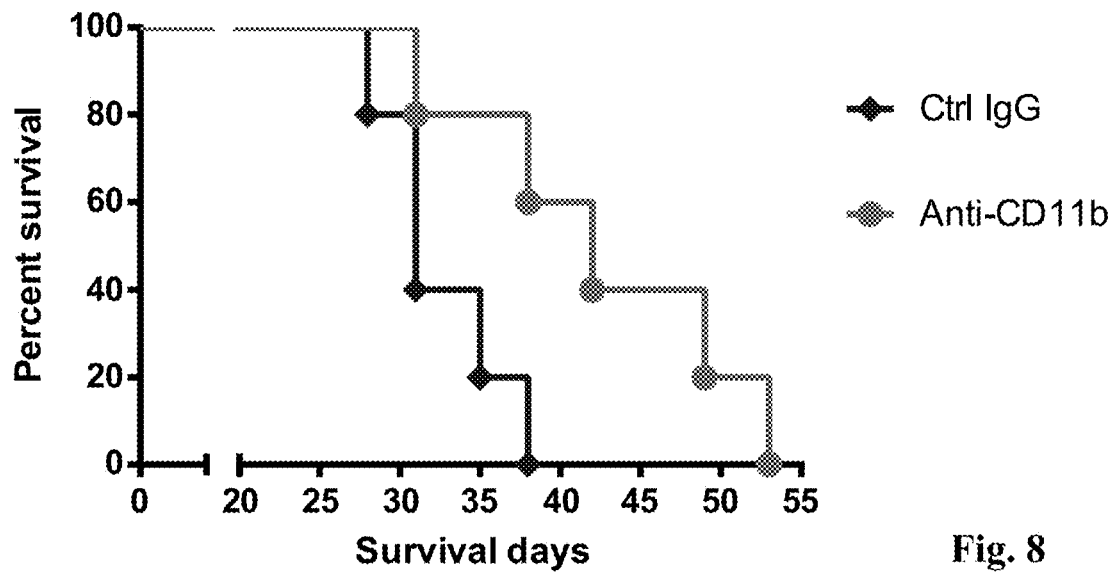
FIG. 8 shows the effects of anti-CD11b antibody monotherapy on survival in LLC1 tumor model. C57BL/6 mice were subcutaneously injected with $1\times10^6$ LLC1 cells at Day 0. On day 7, mice (n=5/group) were injected ip with either control IgG (5 mg/kg) or Rat anti-mouse CD11b antibody. Injections were repeated every three to four days. Mice were analyzed for the effects of anti-CD11b antibody for the long term survival of treated mice in each of the groups.

CD11b binding also demonstrated efficiency in the distinct syngeneic LLC1 tumor model. Treatment with 5 mg/kg of anti-CD11b antibody potently inhibited tumor growth of LLC1 tumor (FIG. 7) and prolong animal survival (FIG. 8) (median survival day Ctrl IgG: 31 day; Anti-CD11b: 42 day).

Figure 9:
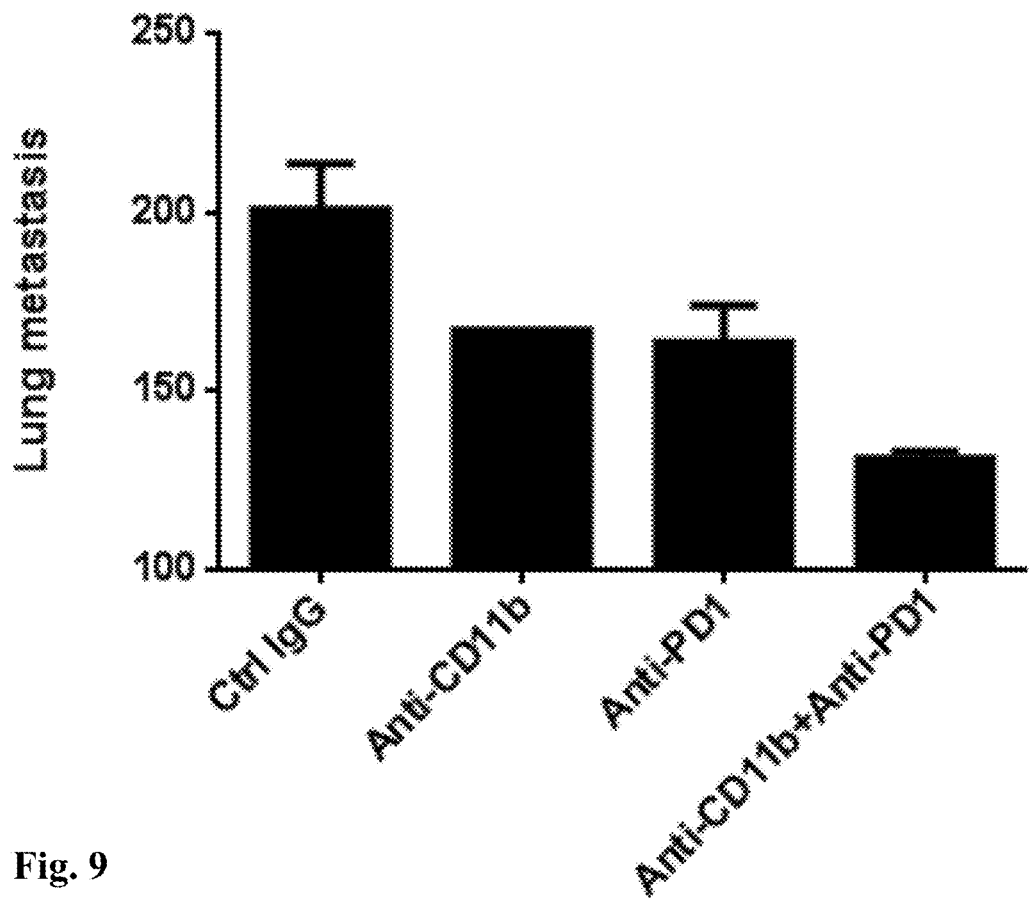
FIG. 9 shows the effect of anti-CD11b antibody and anti-PD1 combination therapy on LLC1 lung metastases model. $1\times10^6$ LLC1 cells were injected into each mouse via tail vein on day 0. On day 1, mice (n=3/group) were injected ip with either control IgG (10 mg/kg), anti-mouse CD11b antibody (10 mg/kg), anti-PD1 antibody (10 mg/kg), or anti-CD11b (10 mg/kg)+anti-PD1 (10 mg/kg). Injections were repeated every three to four day. On day15, mice were sacrificed and the amount of tumor seeding was counted as total numbers of nodules presented in the lungs under microscopy.
Figure 10:
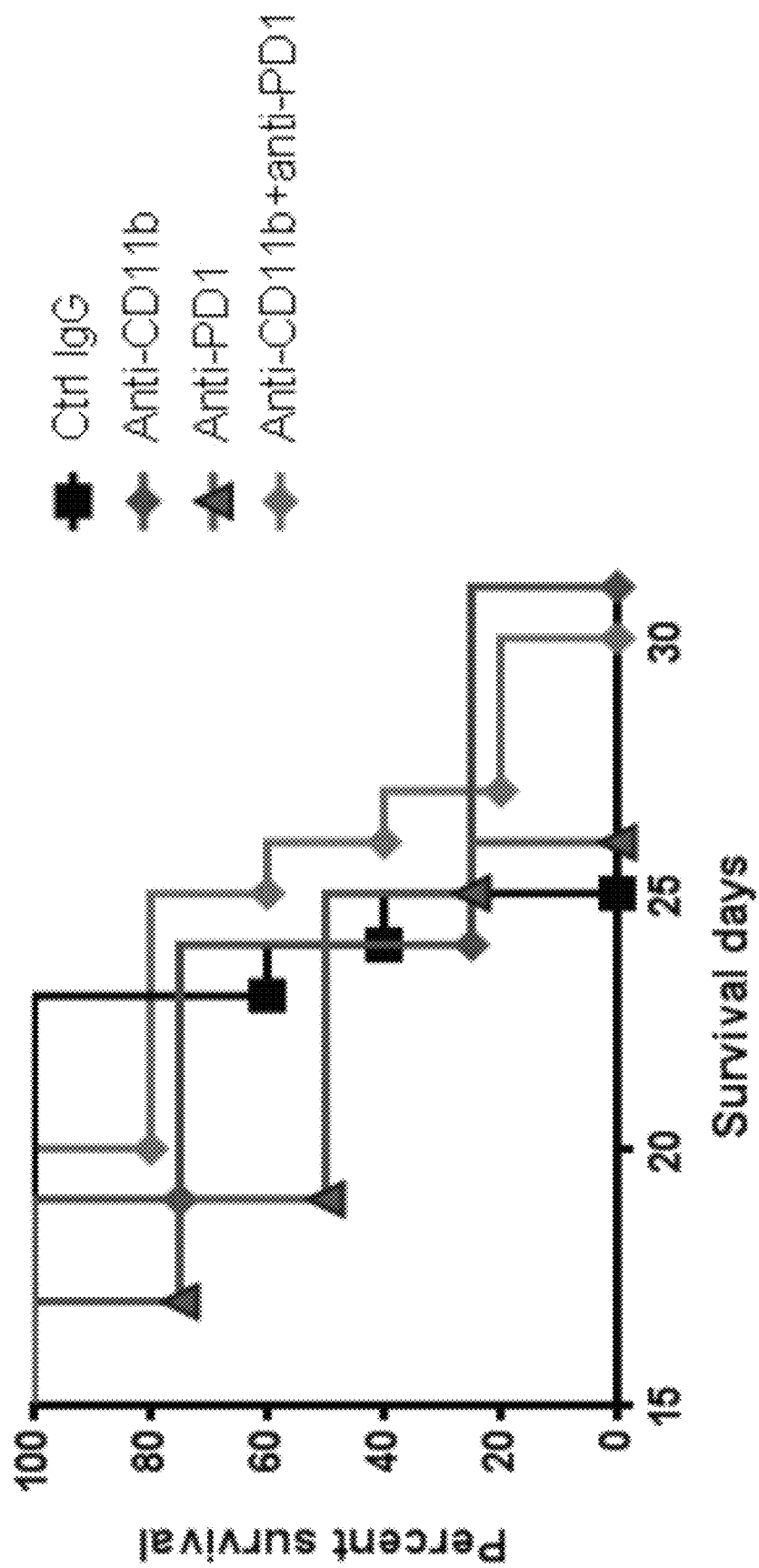
FIG. 10 shows the effect of anti-CD11b antibody and anti-PD1 combination therapy on survival in lung metastases model. $1\times10^6$ LLC1 cells were injected into each mouse via tail vein on day 0. On day 1, mice (n=4-5/group) were injected ip with either control IgG (10 mg/kg), anti-mouse CD11b antibody (10 mg/kg), anti-PD1 antibody (10 mg/kg), or anti-CD11b (10 mg/kg)+anti-PD1 (10 mg/kg). Injections were repeated every three to four day. Mice were analyzed for the effects of combination therapy for the long term survival of treated mice in each of the groups.

Example 3 Synergistic Effect of CD11b Binding and Immune Checkpoint Therapy in Antitumor Immunity The combined treatment demonstrated efficiency in the distinct syngeneic LLC1 lung metastasis model. Treatment with anti-CD11b (10 mg/kg)+anti-PD-1 (10 mg/kg) antibody potently reduced tumor nodule of LLC1 tumor (FIG. 9) (Ctrl IgG vs. anti-CD11b vs. anti-PD-1 vs. anti-CD11b+anti-PD-1=200±13 vs. 167 vs. 164±11 vs. 131±2 on day 15) and prolong animal survival (FIG. 10) (median survival day Ctrl IgG: 24 day; anti-CD11b: 24 day; anti-PD-1: 22 day; anti-CD11b+anti-PD-1: 26 day).

Figure 11:
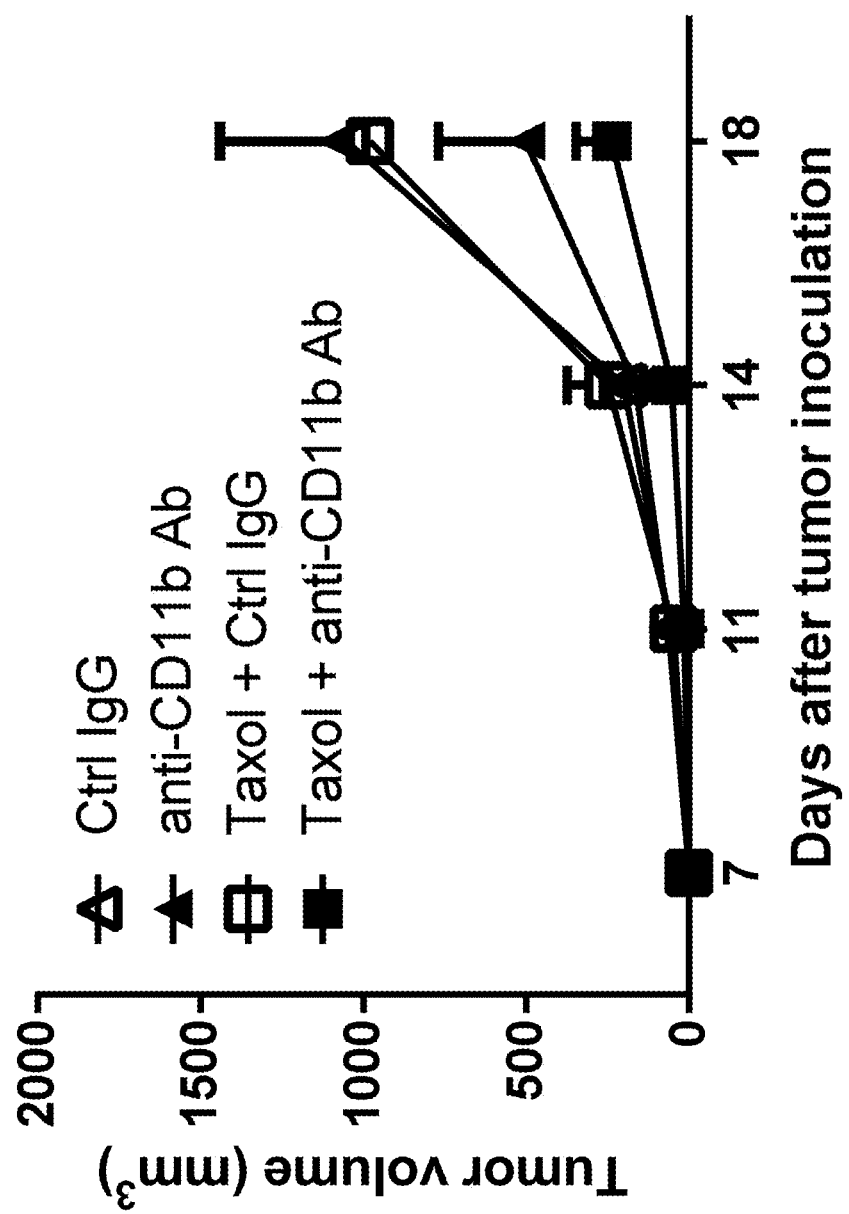
FIG. 11 shows the effect of anti-CD11b antibody and Taxol combination therapy on the growth of B16F10 tumor. C57BL/6 mice were injected subcutaneously with $2\times10^5$ B16F10 cells on day 0. On day7, mice (n=5/group) were injected ip with either control IgG (5 mg/kg), anti-mouse CD11b antibody (5 mg/kg), Taxol (10 mg/kg)+control IgG (5 mg/kg), or Taxol (10 mg/kg)+anti-CD11b antibody (5 mg/kg). Injections were repeated every three to four days. Tumor volumes were measured and the results are presented as the mean±SEM.
Figure 12:
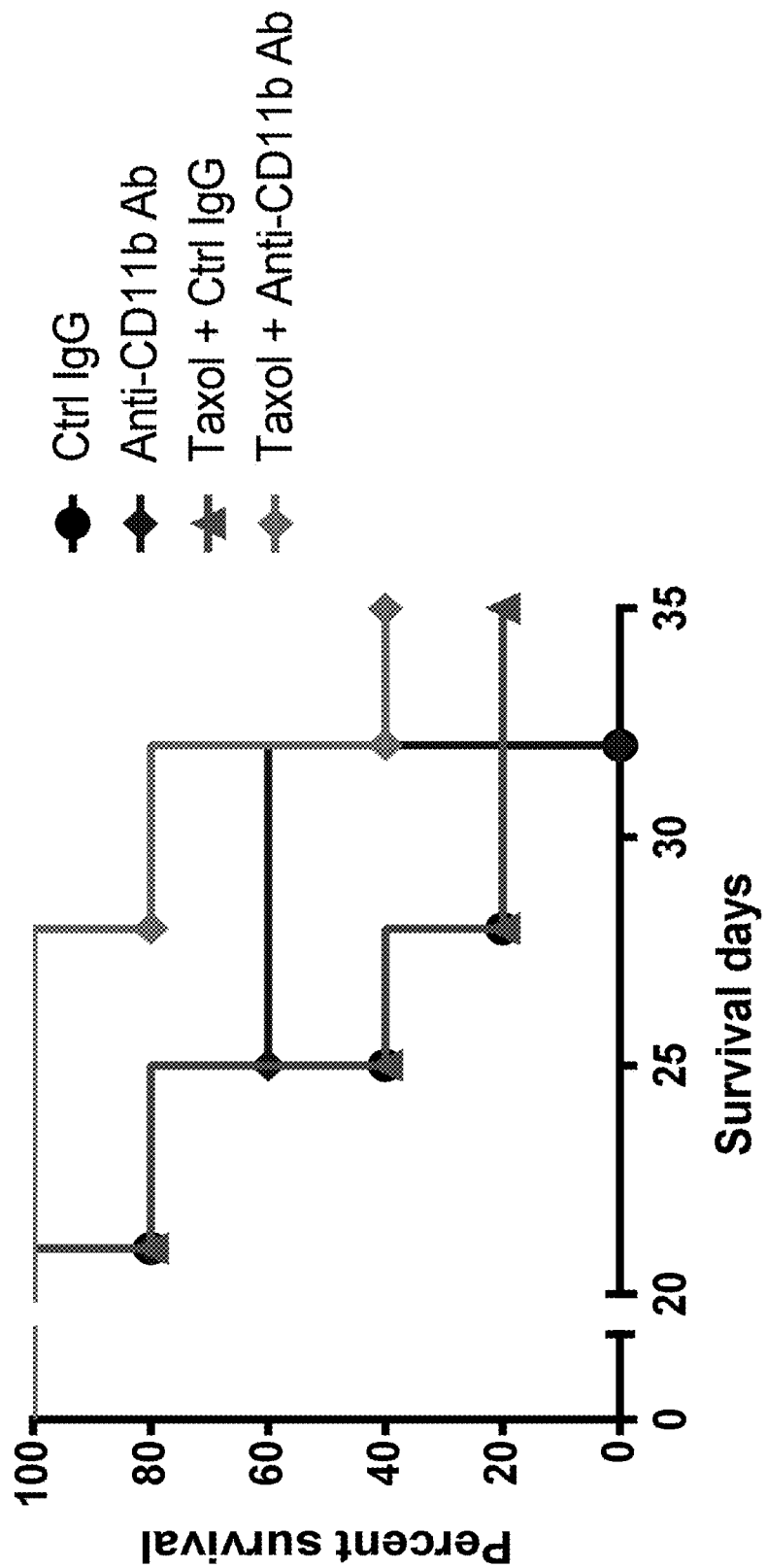
FIG. 12 shows the effect of anti-CD11b antibody and Taxol combination therapy on survival in B16F10 model. C57BL/6 mice were injected subcutaneously with $2 \times 10^5$ B16F10 cells on day 0. On day7, mice (n=5/group) were injected ip with either control IgG (5 mg/kg), anti-mouse CD11 b antibody (5 mg/kg), Taxol (10 mg/kg)+control IgG (5 mg/kg), or Taxol (10 mg/kg)+anti-CD11b (5 mg/kg). Injections were repeated every three to four days. Mice were analyzed for the effects of combination therapy for the long term survival of treated mice in each of the groups.

Example 4 Synergistic Effect of CD11b Binding and Chemotherapy in Antitumor Immunity CD11b binding also enhances chemotherapy. In this example, B16F10 cells were implanted on day 0. On day 7, mice were injected ip with either control IgG (5 mg/kg), anti-mouse CD11b antibody (5 mg/kg), Taxol (10 mg/kg)+control IgG (5 mg/kg), or Taxol (10 mg/kg)+anti-CD11b (5 mg/kg). Injections were repeated every three to four days. As shown in FIG. 11, treatment with a combination of Taxol plus anti-CD11b antibody effectively controlled tumor growth. The effectiveness of the combination treatment was also confirmed in the long term survival (FIG. 12) (median survival day Ctrl IgG: 25 day; anti-CD111b: 32 day; Taxol+Ctrl IgG: 25 day; Taxol+anti-CD11 b: 32 day).

Example 5 in LPS-Induced Immunosuppressed Monocytes or Monocytes from Patients with Septic Shock, Binding CD11b with Anti-CD11b Antibody Also Reduces PD-L1 Expression when Cells are Challenged with LPS Sepsis, a systematic inflammatory response syndrome caused by severe infection, remains a worldwide healthcare problem and a life-threatening disease. It is becoming increasingly clear that sepsis initiates a biphasic immunological reaction that varies over time. During the initial phase of sepsis, a systematic hyperinflammatory immune response can systematically produce inflammatory cytokines, including interleukin (IL)-1, IL-6, and tumor necrosis factor (TNF)-α, which may cause hemodynamic instability, multiorgan dysfunction, coagulation abnormalities, and shock. Concomitant with the hyperinflammatory immune response is a nearly simultaneous production of anti-inflammatory cytokines, including IL-10, and tumor growth factor (TGF)-β; the immune system rapidly enters an immune hyporeactivity state, termed immunoparalysis, which is manifested in an inability to eradicate the primary infection and the development of late nosocomial infections. The indicators of immunoparalysis observed in patients with sepsis include lymphocyte abnormalities, monocytic deactivation with diminished human leukocyte antigen-DR (HLA-DR) surface expression, and low TNF-α production under ex vivo stimulation. Sustained reductions in monocyte HLA-DR expression indicate a high risk for nosocomial infection and death in patients with sepsis. Recently, elevated program death ligand-1 (PD-L1) expression in monocytes in patients with septic shock was observed and was associated with an increased occurrence of secondary nosocomial infections and mortality (Guignant C, Lepape A, Huang X Kherouf H, Denis L, et al. (2011) *Programmed death-1 levels correlate with increased mortality, nosocomial infection and immune dysfunctions in septic shock patients. Crit Care* 15: R99). Therefore, the level of PD-L1 expression in monocytes may serve as a new marker for immunoparalysis.

Figure 13:
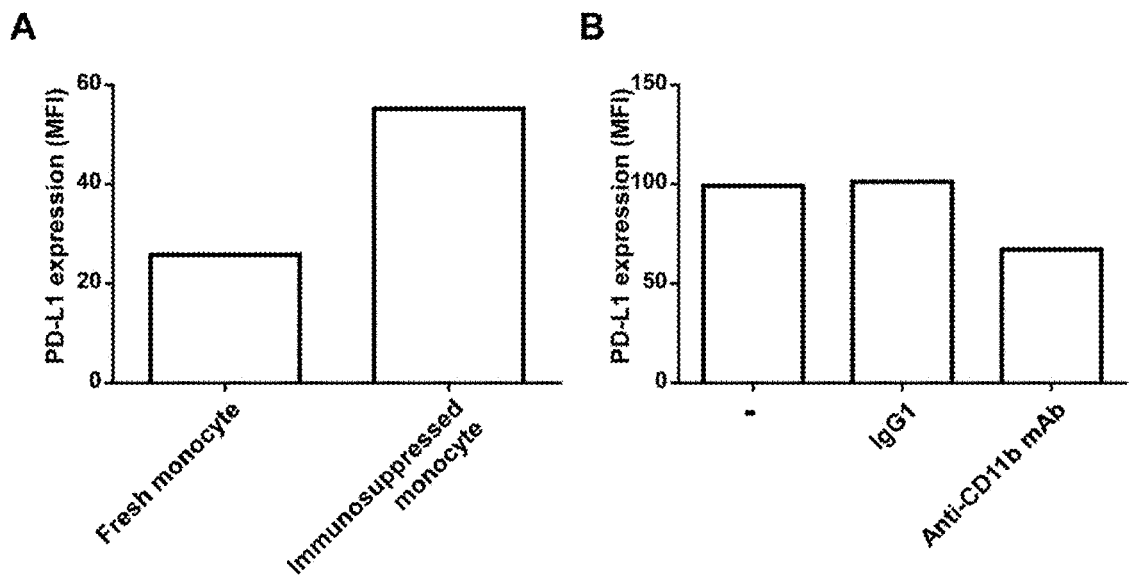
FIG. 13 shows that binding CD11b with anti-CD11b antibody reduces PD-L1 expression in LPS-induced immunosuppressed monocytes challenged with 1 µg/ml LPS. (A) Human monocytes were isolated from healthy volunteers and pre-treated with 100 ng/ml LPS for 2 days to induce immunosuppression. (B) LPS-induced immunosuppressed monocytes were challenge with 1 µg/ml LPS for 18 hr in the presence of 10 µg/ml IgG1 or anti-CD11b antibody (ICRF44). Treated cells were washed and analyzed by flow cytometry. Surface PD-L1 expression is presented as the MFI.
Figure 14:
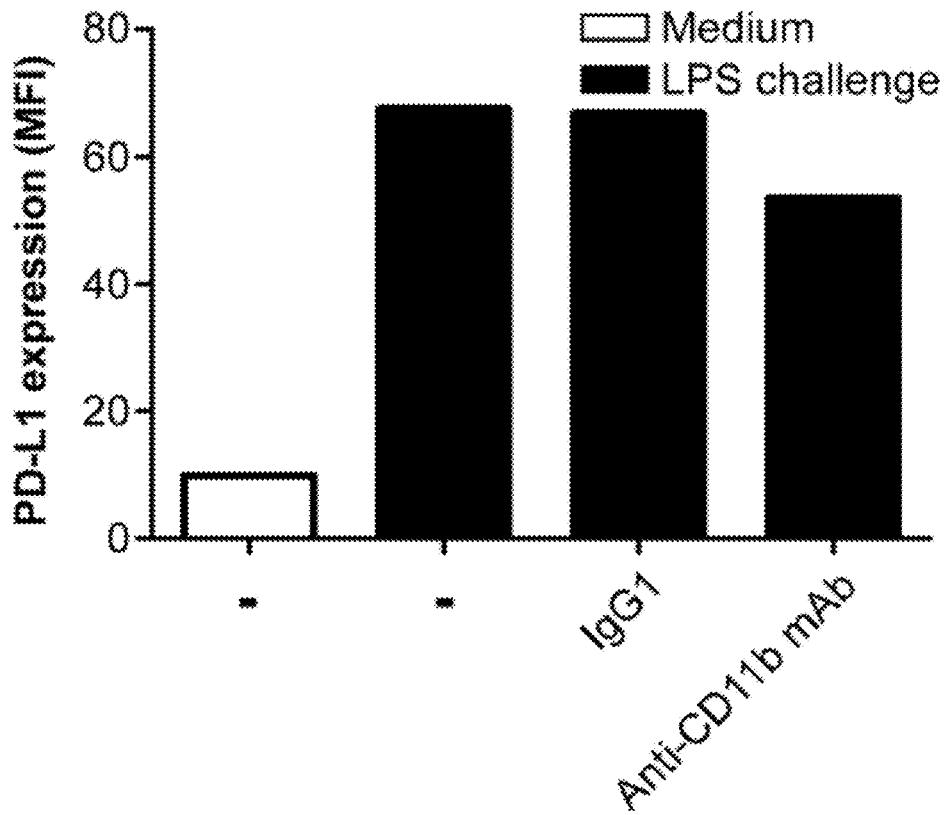
FIG. 14 shows that binding CD11b with anti-CD11b antibody reduces PD-L1 expression in human monocytes from patients with septic shock when challenged with 1 µg/ml LPS. Human monocytes were isolated from patient with septic shock and challenged with 1 µg/ml LPS for 18 hr in the presence of 10 µg/ml IgG1 or anti-CD11b antibody. Treated cells were washed and analyzed by flow cytometry. Surface PD-L1 expression is presented as the MFI.

It has been report that prior exposure of monocytes to LPS over 2 days would cause them to become immunosuppressed monocytes (Wolk K, Docke W D, von Baehr V Volk H D, and Sabat R. (2000) *Impaired antigen presentation by human monocytes during endotoxin tolerance. Blood* 96: 218). Clinically, these cells are associated with immunoparalysis and mortality. We established reproducible LPS-induced immunosuppressed monocytes, in which human monocytes are preincubated with 100 ng/ml LPS for 2 days. Compare with fresh isolated human monocytes, LPS-induced immunosuppressed monocytes expressed higher PD-L1 levels on the cell surface (FIG. 13A). To examine the effect of CD11b modulators in LPS-induced immunosuppressed monocytes, cells were exposed to 1 μg/ml LPS for 18 hr in the presence of IgG1 or anti-CD11b antibody (ICRF44). As shown in FIG. 13B, binding CD11b with anti-CD11b antibody (ICRF44) reduced the PD-L1 expression in LPS-induced immunosuppressed monocytes when cells challenged with LPS. Moreover, anti-CD11b antibody (ICRF44) treatment also reduced PD-L1 expression in monocytes from patients with septic shock upon in vitro LPS stimulation (FIG. 14).

Example 6 Humanized Antibodies that Bind Human CD11b

The variable domain sequences of murine anti-human CD11b antibody were searched against the human antibody database. 10 sets of human framework sequences with high homology to murine anti-human CD11b were chosen as human acceptors for both light and heavy chains. Meanwhile, N-glycosylation motifs were analyzed. Potential glycosylation sites in the candidate human variable regions should therefore be avoided. The humanized variable domains of 10 light chains were denoted as VL1, VL2, VL3, VL4, V$_L$5, LC1, LC2, LC3, LC4, and LC5 (FIG. 15); while the humanized variable domains of 10 heavy chains were denoted as VH1, VH2, VH3, VH4, VH5, HC1, HC2, HC3, HC4, and HC5 (FIG. 16). These light chain and heavy chain peptide sequence may provide humanized antibodies or antigen-binding portions that bind to human anti-CD11b with high affinity.

Example 7 Functional Activity of Humanized CD11b Antibody

Figure 17:
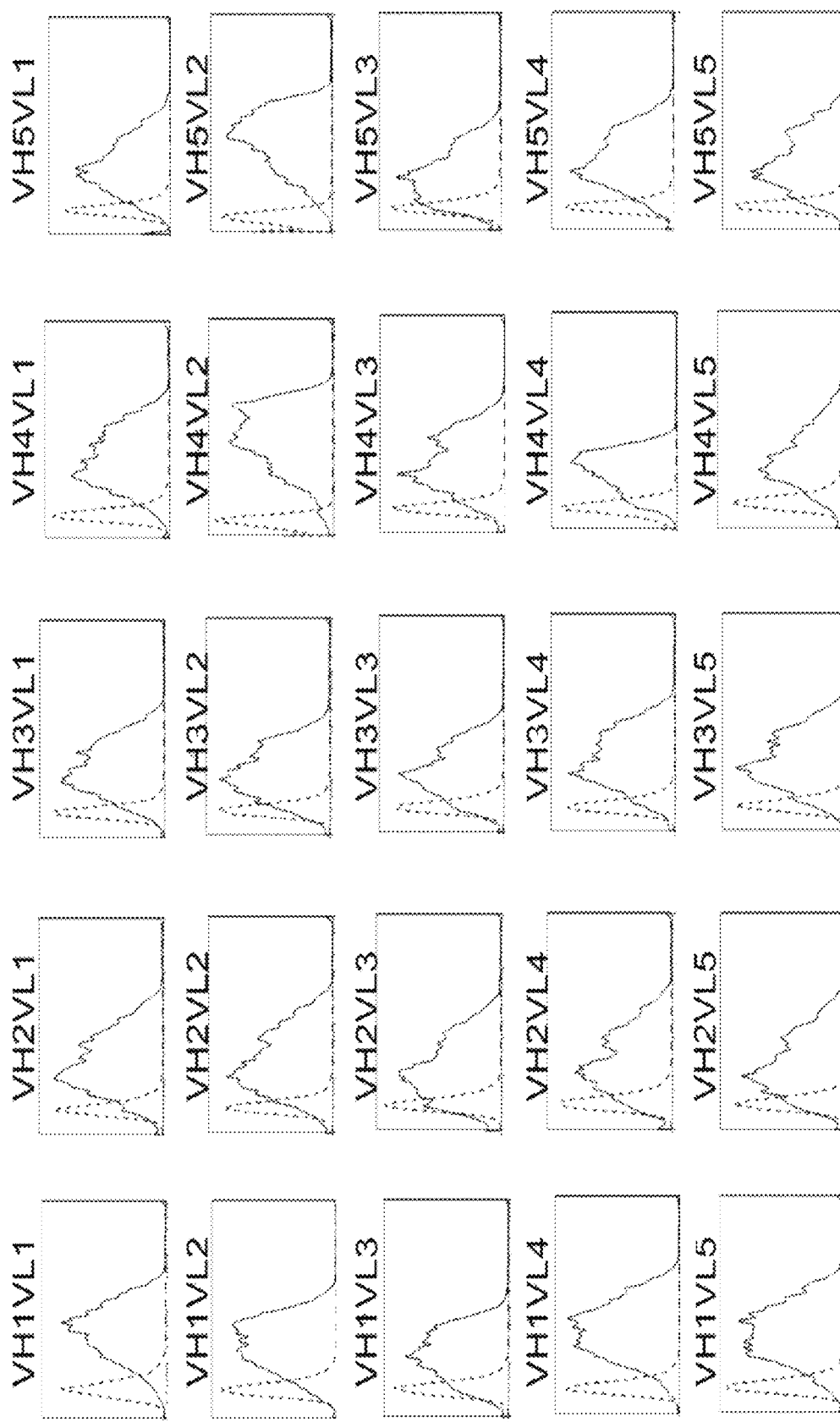
FIG. 17 shows the binding activities of humanized anti-CD11b antibodies. K562 cells or cells transfected with human CD11b (K562/CD11b) were incubated with 10 µg/ml humanized anti-CD11b antibodies for 30 mins. Bound Ab was detected by FITC-conjugated mouse anti-human IgG. The cells were analyzed by flow cytometry. Dash line represents antibodies bound the K562 cells. Solid line represents antibodies bind to K562/CD11b cells.

The specificity of humanized anti-CD11b antibodies were determined by flow cytometry using K562 cells expressing CD11b. As shown in FIG. 17, all humanized anti-CD11b antibodies in this example were able to bind to the CD11b transfected K562 cells. In contrast, these antibodies did not bind to K562 cells. Taken together, these results demonstrate that the humanized anti-CD11b antibodies can specifically bind to the CD11b epitope.

Figure 18:
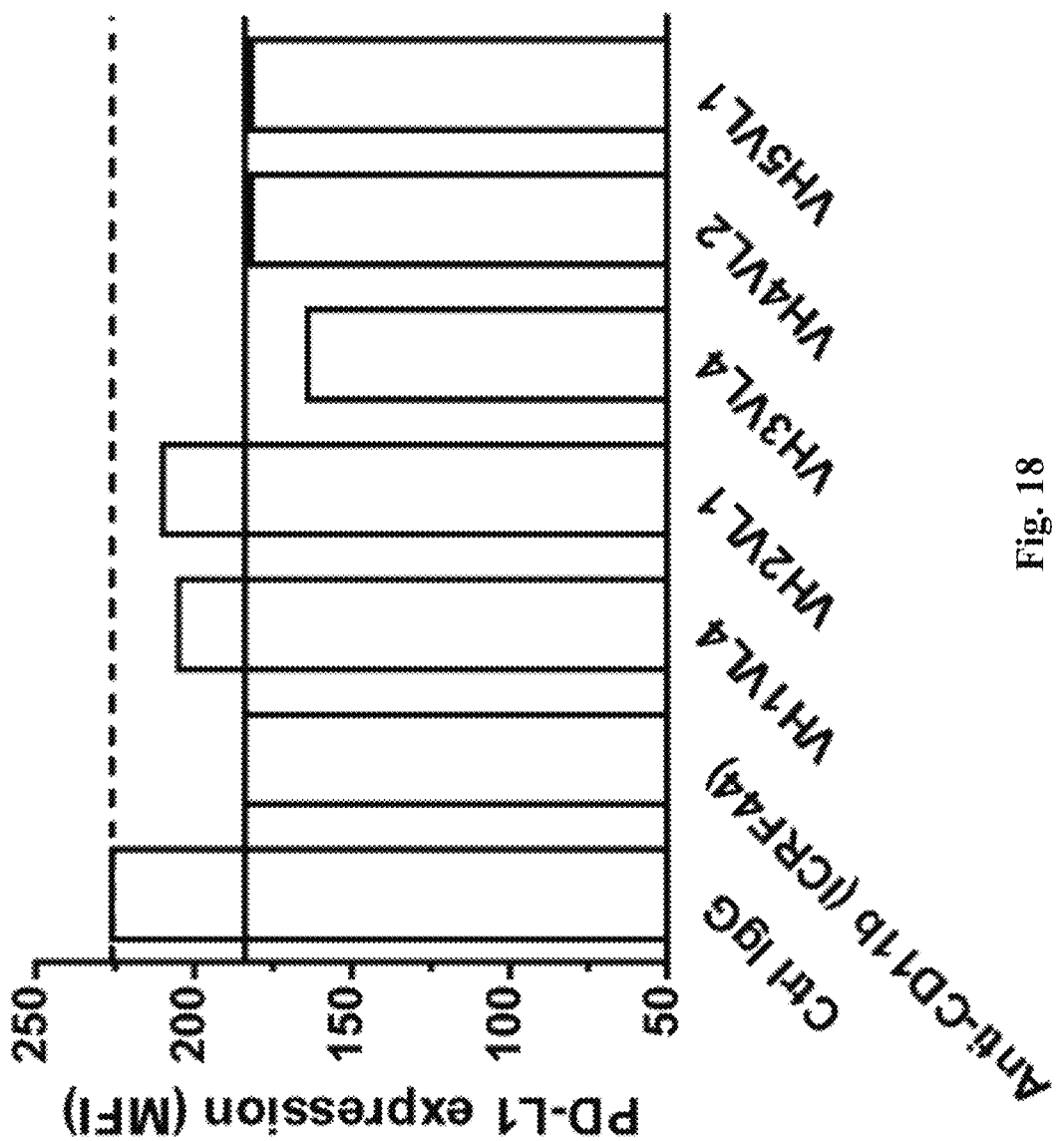
FIG. 18 shows binding CD11b with anti-CD11b antibodies reduces PD-L1 expression in LPS-primed human monocytes. Primed-monocytes were incubated in the presence of either an isotype control IgG, anti-CD11b antibody (ICRF44) or humanized anti-CD11b antibodies for 18 hr. The cells were harvested and PD-L1 expression on monocytes was analyzed using flow cytometry.

To examine the functional activity of humanized anti-CD11b antibody, the antibody was used in LPS-primed monocytes that measure the ability of the antibody to inhibit PD-L1 expression on the surface of monocytes. As shown in FIG. 18, the upregulation of PD-L1 by LPS can be significantly reduced by the humanized anti-CD11b antibodies.

In summary, we described a series of humanized anti-CD11b antibodies directed against the human αM domain. Binding of humanized anti-CD11b antibodies was able to reduce PD-L1 expression on LPS-primed monocytes.

---

What is claimed is:

1. A method of treating a disease associated with immune suppression, comprising administering a composition to a subject in need thereof, inhibiting PD-L1 expression, and reversing immune suppression or immune exhaustion in the subject, thereby treating a disease associated with immune suppression, wherein the composition comprises an antibody or antigen-binding portion thereof comprising:
   (i) a heavy chain variable region comprising H-CDR1 having the sequence of SEQ ID NO:1, H-CDR2 having the sequence of SEQ ID NO:3, and H-CDR3 having the sequence of SEQ ID NO:5; or a heavy chain variable region comprising H-CDR1 having the sequence of SEQ ID NO:2, H-CDR2 having the sequence of SEQ ID NO:4, and H-CDR3 having the sequence of SEQ ID NO:6; and
   (ii) a light chain variable region comprising L-CDR1 having the sequence of SEQ ID NO:7, L-CDR2 having the sequence of SEQ ID NO:9, and L-CDR3 having the sequence of SEQ ID NO:11; or a light chain variable region comprising L-CDR1 having the sequence of SEQ ID NO:8, L-CDR2 having the sequence of SEQ ID NO:10, and L-CDR3 having the sequence of SEQ ID NO:12.

2. The method according to claim 1, wherein the antibody or the antigen-binding portion thereof comprises:
   a heavy chain variable region comprising the amino acid sequence of one of SEQ ID NO:13-SEQ ID NO:22, and
   a light chain variable region comprising the amino acid sequence of one of SEQ ID NO:23-SEQ ID NO:32.

3. The method according to claim 1, wherein the antibody or the antigen-binding portion thereof comprises:
   (a) a heavy chain variable region comprising the amino acid sequence of SEQ ID NO:13, and a light chain variable region comprising the amino acid sequence of SEQ ID NO:23; or
   (b) a heavy chain variable region comprising the amino acid sequence of SEQ ID NO:14, and a light chain variable region comprising the amino acid sequence of SEQ ID NO:24; or
   (c) a heavy chain variable region comprising the amino acid sequence of SEQ ID NO:15, and a light chain variable region comprising the amino acid sequence of SEQ ID NO:25; or
   (d) a heavy chain variable region comprising the amino acid sequence of SEQ ID NO:16, and a light chain variable region comprising the amino acid sequence of SEQ ID NO:26; or
   (e) a heavy chain variable region comprising the amino acid sequence of SEQ ID NO:17, and a light chain variable region comprising the amino acid sequence of SEQ ID NO:27; or
   (f) a heavy chain variable region comprising the amino acid sequence of SEQ ID NO:18, and a light chain variable region comprising the amino acid sequence of SEQ ID NO:28; or
   (g) a heavy chain variable region comprising the amino acid sequence of SEQ ID NO:19, and a light chain variable region comprising the amino acid sequence of SEQ ID NO:29; or
   (h) a heavy chain variable region comprising the amino acid sequence of SEQ ID NO:20, and a light chain variable region comprising the amino acid sequence of SEQ ID NO:30; or
   (i) a heavy chain variable region comprising the amino acid sequence of SEQ ID NO:21, and a light chain variable region comprising the amino acid sequence of SEQ ID NO:31; or
   (j) a heavy chain variable region comprising the amino acid sequence of SEQ ID NO:22, and a light chain variable region comprising the amino acid sequence of SEQ ID NO:32.

4. The method according to claim 1, further comprising administering to the subject an agent that can modulate an immune checkpoint or a chemotherapeutic agent.

5. The method according to claim 4, wherein the agent that can modulate an immune checkpoint is an anti-PD-1 antibody, a PD-1 ligand, an anti-PD-L1 antibody, a PD-L1 ligand, an anti-CTLA-4 antibody, a CTLA-4 ligand, or a binding fragment thereof.

6. The method according to claim 1, wherein the immunosuppression or immune exhaustion is an acute and/or chronic infection, sepsis, cancer, or immunosenescence in aging.

7. The method according to claim 6, wherein the cancer is one selected from the group consisting of melanoma, lung cancer, squamous cell carcinomas of the lung, head and neck cancer, breast cancer, ovarian cancer, uterine cancer, prostate cancer, gastric carcinoma, cervical cancer, esophageal carcinoma, bladder cancer, kidney cancer, brain cancer, liver cancer, colon cancer, bone cancer, pancreatic cancer, skin cancer, cutaneous or intraocular malignant melanoma, ovarian cancer, rectal cancer, cancer of the anal region, stomach cancer, testicular cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, esophagus cancer, small intestine cancer, endocrine system cancer, thyroid gland cancer, parathyroid gland cancer, adrenal gland cancer, sarcoma of soft tissue, urethra cancer, penis cancer, chronic or acute leukemias including acute myeloid leukemia, chronic myeloid leukemia, acute lymphoblastic leukemia, chronic lymphocytic leukemia, solid tumors of childhood, lymphocytic lymphoma, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, and T-cell lymphoma.

8. A method for reversing immune suppression or immune exhaustion in a subject in need thereof, comprising: administering an antibody or an antigen-binding portion thereof, thereby reversing immune suppression or immune exhaustion in the subject, wherein the antibody or antigen-binding portion thereof comprises:
   (i) a heavy chain variable region comprising H-CDR1 having the sequence of SEQ ID NO:1, H-CDR2 having the sequence of SEQ ID NO:3, and H-CDR3 having the sequence of SEQ ID NO:5; or a heavy chain variable region comprising H-CDR1 having the sequence of SEQ ID NO:2, H-CDR2 having the sequence of SEQ ID NO:4, and H-CDR3 having the sequence of SEQ ID NO:6; and
   (ii) a light chain variable region comprising L-CDR1 having the sequence of SEQ ID NO:7, L-CDR2 having the sequence of SEQ ID NO:9, and L-CDR3 having the sequence of SEQ ID NO:11; or a light chain variable region comprising L-CDR1 having the sequence of SEQ ID NO:8, L-CDR2 having the sequence of SEQ ID NO:10, and L-CDR3 having the sequence of SEQ ID NO:12.

9. The method according to claim 8, wherein the antibody or the antigen-binding portion thereof comprises:
a heavy chain variable region comprising the amino acid sequence of one of SEQ ID NO:13-SEQ ID NO:22, and a light chain variable region comprising the amino acid sequence of one of SEQ ID NO:23-SEQ ID NO:32.

10. The method according to claim 8, wherein the antibody or the antigen-binding portion thereof comprises:
(a) a heavy chain variable region comprising the amino acid sequence of SEQ ID NO:13, and a light chain variable region comprising the amino acid sequence of SEQ ID NO:23; or
(b) a heavy chain variable region comprising the amino acid sequence of SEQ ID NO:14, and a light chain variable region comprising the amino acid sequence of SEQ ID NO:24; or
(c) a heavy chain variable region comprising the amino acid sequence of SEQ ID NO:15, and a light chain variable region comprising the amino acid sequence of SEQ ID NO:25; or
(d) a heavy chain variable region comprising the amino acid sequence of SEQ ID NO:16, and a light chain variable region comprising the amino acid sequence of SEQ ID NO:26; or
(e) a heavy chain variable region comprising the amino acid sequence of SEQ ID NO:17, and a light chain variable region comprising the amino acid sequence of SEQ ID NO:27; or
(f) a heavy chain variable region comprising the amino acid sequence of SEQ ID NO:18, and a light chain variable region comprising the amino acid sequence of SEQ ID NO:28; or
(g) a heavy chain variable region comprising the amino acid sequence of SEQ ID NO:19, and a light chain variable region comprising the amino acid sequence of SEQ ID NO:29; or
(h) a heavy chain variable region comprising the amino acid sequence of SEQ ID NO:20, and a light chain variable region comprising the amino acid sequence of SEQ ID NO:30; or
(i) a heavy chain variable region comprising the amino acid sequence of SEQ ID NO:21, and a light chain variable region comprising the amino acid sequence of SEQ ID NO:31; or
(j) a heavy chain variable region comprising the amino acid sequence of SEQ ID NO:22, and a light chain variable region comprising the amino acid sequence of SEQ ID NO:32.

11. The method according to claim 8, further comprising administering to the subject an agent that can modulate an immune checkpoint or a chemotherapeutic agent.

12. The method according to claim 11, wherein the agent that can modulate an immune checkpoint is an anti-PD-1 antibody, a PD-1 ligand, an anti-PD-L1 antibody, a PD-L1 ligand, an anti-CTLA-4 antibody, a CTLA-4 ligand, or a binding fragment thereof.

13. The method according to claim 8, wherein the immunosuppression or immune exhaustion is an acute and/or chronic infection, sepsis, cancer, or immunosenescence in aging.

* * * * *

SEQUENCE LISTING

<160> NUMBER OF SEQ ID NOS: 32

<210> SEQ ID NO 1
<211> LENGTH: 5
<212> TYPE: PRT
<213> ORGANISM: Artificial
<220> FEATURE:
<223> OTHER INFORMATION: H-CDR1

<400> SEQUENCE: 1

Asn Tyr Trp Ile Asn
1               5

<210> SEQ ID NO 2
<211> LENGTH: 10
<212> TYPE: PRT
<213> ORGANISM: artificial
<220> FEATURE:
<223> OTHER INFORMATION: H-CDR1

<400> SEQUENCE: 2

Gly Phe Ser Leu Thr Ser Asn Ser Ile Ser
1               5                   10

<210> SEQ ID NO 3
<211> LENGTH: 17
<212> TYPE: PRT
<213> ORGANISM: artificial
<220> FEATURE:
<223> OTHER INFORMATION: H-CDR2

<400> SEQUENCE: 3

Asn Ile Tyr Pro Ser Asp Thr Tyr Ile Asn His Asn Gln Lys Phe Lys
1               5                   10                  15

Asp

<210> SEQ ID NO 4
<211> LENGTH: 16
<212> TYPE: PRT
<213> ORGANISM: artificial
<220> FEATURE:
<223> OTHER INFORMATION: H-CDR2

<400> SEQUENCE: 4

```
Ala Ile Trp Ser Gly Gly Gly Thr Asp Tyr Asn Ser Asp Leu Lys Ser
1               5                   10                  15

<210> SEQ ID NO 5
<211> LENGTH: 9
<212> TYPE: PRT
<213> ORGANISM: artificial
<220> FEATURE:
<223> OTHER INFORMATION: H-CDR3

<400> SEQUENCE: 5

Ser Ala Tyr Ala Asn Tyr Phe Asp Tyr
1               5

<210> SEQ ID NO 6
<211> LENGTH: 10
<212> TYPE: PRT
<213> ORGANISM: artificial
<220> FEATURE:
<223> OTHER INFORMATION: H-CDR3

<400> SEQUENCE: 6

Arg Gly Gly Tyr Pro Tyr Tyr Phe Asp Tyr
1               5                   10

<210> SEQ ID NO 7
<211> LENGTH: 11
<212> TYPE: PRT
<213> ORGANISM: artificial
<220> FEATURE:
<223> OTHER INFORMATION: L-CDR1

<400> SEQUENCE: 7

Arg Ala Ser Gln Asn Ile Gly Thr Ser Ile His
1               5                   10

<210> SEQ ID NO 8
<211> LENGTH: 17
<212> TYPE: PRT
<213> ORGANISM: artificial
<220> FEATURE:
<223> OTHER INFORMATION: L-CDR1

<400> SEQUENCE: 8

Lys Ser Ser Gln Ser Leu Leu Tyr Ser Glu Asn Gln Glu Asn Tyr Leu
1               5                   10                  15
Ala

<210> SEQ ID NO 9
<211> LENGTH: 7
<212> TYPE: PRT
<213> ORGANISM: artificial
<220> FEATURE:
<223> OTHER INFORMATION: L-CDR2

<400> SEQUENCE: 9

Tyr Ala Ser Glu Ser Ile Ser
1               5

<210> SEQ ID NO 10
<211> LENGTH: 7
<212> TYPE: PRT
<213> ORGANISM: artificial
<220> FEATURE:
<223> OTHER INFORMATION: L-CDR2

<400> SEQUENCE: 10
```

Trp Ala Ser Thr Arg Gln Ser
1               5

<210> SEQ ID NO 11
<211> LENGTH: 10
<212> TYPE: PRT
<213> ORGANISM: artificial
<220> FEATURE:
<223> OTHER INFORMATION: L-CDR3

<400> SEQUENCE: 11

Gln Gln Ser Asp Ser Trp Pro Thr Leu Thr
1               5                   10

<210> SEQ ID NO 12
<211> LENGTH: 9
<212> TYPE: PRT
<213> ORGANISM: artificial
<220> FEATURE:
<223> OTHER INFORMATION: L-CDR3

<400> SEQUENCE: 12

Gln Gln Tyr Tyr Asp Thr Pro Leu Thr
1               5

<210> SEQ ID NO 13
<211> LENGTH: 118
<212> TYPE: PRT
<213> ORGANISM: artificial
<220> FEATURE:
<223> OTHER INFORMATION: Heavy chain variable region of the humanized
      anti-CD11b antibodies-VH1

<400> SEQUENCE: 13

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Ile Asn Trp Val Arg Gln Ala Pro Gly Gln Gly Leu Glu Trp Met
        35                  40                  45

Gly Asn Ile Tyr Pro Ser Asp Thr Tyr Ile Asn His Asn Gln Lys Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Ala Tyr Ala Asn Tyr Phe Asp Tyr Trp Gly Gln Gly Thr
            100                 105                 110

Leu Val Thr Val Ser Ser
        115

<210> SEQ ID NO 14
<211> LENGTH: 118
<212> TYPE: PRT
<213> ORGANISM: artificial
<220> FEATURE:
<223> OTHER INFORMATION: Heavy chain variable region of the humanized
      anti-CD11b antibodies-VH2

<400> SEQUENCE: 14

Gln Val Gln Leu Val Gln Ser Gly Ala Glu Val Lys Lys Pro Gly Ser
1               5                   10                  15

```
Ser Val Lys Val Ser Cys Lys Ala Ser Gly Thr Phe Ser Asn Tyr
            20                  25                  30

Trp Ile Asn Trp Val Arg Gln Ala Pro Gly Gln Gly Leu Glu Trp Met
            35                  40                  45

Gly Asn Ile Tyr Pro Ser Asp Thr Tyr Ile Asn His Asn Gln Lys Phe
        50                  55                  60

Lys Asp Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                85                  90                  95

Ala Thr Ser Ala Tyr Ala Asn Tyr Phe Asp Tyr Trp Gly Gln Gly Thr
                100                 105                 110

Leu Val Thr Val Ser Ser
            115

<210> SEQ ID NO 15
<211> LENGTH: 118
<212> TYPE: PRT
<213> ORGANISM: artificial
<220> FEATURE:
<223> OTHER INFORMATION: Heavy chain variable region of the humanized
      anti-CD11b antibodies-VH3

<400> SEQUENCE: 15

Gln Val Gln Leu Val Gln Ser Gly Ala Glu Val Lys Lys Pro Gly Ala
 1               5                   10                  15

Ser Val Lys Val Ser Cys Lys Ala Ser Gly Tyr Thr Phe Thr Asn Tyr
            20                  25                  30

Trp Ile Asn Trp Val Arg Gln Ala Thr Gly Gln Gly Leu Glu Trp Met
            35                  40                  45

Gly Asn Ile Tyr Pro Ser Asp Thr Tyr Ile Asn His Asn Gln Lys Phe
        50                  55                  60

Lys Asp Arg Val Thr Met Thr Arg Asn Thr Ser Ile Ser Thr Ala Tyr
 65                  70                  75                  80

Met Glu Leu Ser Ser Leu Arg Ser Glu Asp Thr Ala Val Tyr Tyr Cys
                85                  90                  95

Ala Arg Ser Ala Tyr Ala Asn Tyr Phe Asp Tyr Trp Gly Gln Gly Thr
                100                 105                 110

Leu Val Thr Val Ser Ser
            115

<210> SEQ ID NO 16
<211> LENGTH: 118
<212> TYPE: PRT
<213> ORGANISM: artificial
<220> FEATURE:
<223> OTHER INFORMATION: Heavy chain variable region of the humanized
      anti-CD11b antibodies-VH4

<400> SEQUENCE: 16

Gln Val Gln Leu Val Gln Ser Gly Ala Glu Val Lys Lys Pro Gly Ala
 1               5                   10                  15

Ser Val Lys Val Ser Cys Lys Ala Ser Gly Tyr Thr Phe Thr Asn Tyr
            20                  25                  30

Trp Ile Asn Trp Val Arg Gln Ala Pro Gly Gln Arg Leu Glu Trp Met
            35                  40                  45

Gly Asn Ile Tyr Pro Ser Asp Thr Tyr Ile Asn His Asn Gln Lys Phe
        50                  55                  60
```

```
Lys Asp Arg Val Thr Ile Thr Arg Asp Thr Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ser Ala Tyr Ala Asn Tyr Phe Asp Tyr Trp Gly Gln Gly Thr
            100                 105                 110

Leu Val Thr Val Ser Ser
        115
```

<210> SEQ ID NO 17
<211> LENGTH: 118
<212> TYPE: PRT
<213> ORGANISM: artificial
<220> FEATURE:
<223> OTHER INFORMATION: Heavy chain variable region of the humanized
    anti-CD11b antibodies-VH5

<400> SEQUENCE: 17

```
Gln Val Gln Leu Val Gln Ser Gly Ala Glu Val Lys Lys Pro Gly Ala
 1               5                  10                  15

Thr Val Lys Ile Ser Cys Lys Val Ser Gly Tyr Thr Phe Thr Asn Tyr
             20                  25                  30

Trp Ile Asn Trp Val Gln Gln Ala Pro Gly Lys Gly Leu Glu Trp Met
         35                  40                  45

Gly Asn Ile Tyr Pro Ser Asp Thr Tyr Ile Asn His Asn Gln Lys Phe
     50                  55                  60

Lys Asp Arg Val Thr Ile Thr Ala Asp Thr Ser Thr Asp Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ser Ala Tyr Ala Asn Tyr Phe Asp Tyr Trp Gly Gln Gly Thr
            100                 105                 110

Leu Val Thr Val Ser Arg
        115
```

<210> SEQ ID NO 18
<211> LENGTH: 117
<212> TYPE: PRT
<213> ORGANISM: artificial
<220> FEATURE:
<223> OTHER INFORMATION: Heavy chain variable region of the humanized
    anti-CD11b antibodies-HC1

<400> SEQUENCE: 18

```
Gln Val Gln Leu Gln Glu Ser Gly Pro Gly Leu Val Lys Pro Ser Glu
 1               5                  10                  15

Thr Leu Ser Leu Thr Cys Thr Val Ser Gly Phe Ser Leu Thr Ser Asn
             20                  25                  30

Ser Ile Ser Trp Ile Arg Gln Pro Pro Gly Lys Gly Leu Glu Trp Ile
         35                  40                  45

Gly Ala Ile Trp Ser Gly Gly Thr Asp Tyr Asn Ser Asp Leu Lys
     50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Gly Gly Tyr Pro Tyr Tyr Phe Asp Tyr Trp Gly Gln Gly Thr Leu
            100                 105                 110
```

Val Thr Val Ser Ser
        115

<210> SEQ ID NO 19
<211> LENGTH: 117
<212> TYPE: PRT
<213> ORGANISM: artificial
<220> FEATURE:
<223> OTHER INFORMATION: Heavy chain variable region of the humanized
      anti-CD11b antibodies-HC2

<400> SEQUENCE: 19

Gln Val Gln Leu Gln Glu Ser Gly Pro Gly Leu Val Lys Pro Ser Gly
1               5                   10                  15

Thr Leu Ser Leu Thr Cys Ala Val Tyr Gly Phe Ser Leu Thr Ser Asn
            20                  25                  30

Ser Ile Ser Trp Ile Arg Gln Pro Pro Gly Lys Gly Leu Glu Trp Ile
        35                  40                  45

Gly Ala Ile Trp Ser Gly Gly Gly Thr Asp Tyr Asn Ser Asp Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Gly Tyr Pro Tyr Tyr Phe Asp Tyr Trp Gly Gln Gly Thr Met
            100                 105                 110

Val Thr Val Ser Ser
        115

<210> SEQ ID NO 20
<211> LENGTH: 117
<212> TYPE: PRT
<213> ORGANISM: artificial
<220> FEATURE:
<223> OTHER INFORMATION: Heavy chain variable region of the humanized
      anti-CD11b antibodies-HC3

<400> SEQUENCE: 20

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Phe Ser Leu Thr Ser Asn
            20                  25                  30

Ser Ile Ser Trp Ile Arg Gln Pro Pro Gly Lys Gly Leu Glu Trp Ile
        35                  40                  45

Gly Ala Ile Trp Ser Gly Gly Gly Thr Asp Tyr Asn Ser Asp Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Gly Tyr Pro Tyr Tyr Phe Asp Tyr Trp Gly Gln Gly Thr Leu
            100                 105                 110

Val Thr Val Ser Ser
        115

<210> SEQ ID NO 21
<211> LENGTH: 117
<212> TYPE: PRT
<213> ORGANISM: artificial
<220> FEATURE:

<223> OTHER INFORMATION: Heavy chain variable region of the humanized
    anti-CD11b antibodies-HC4

<400> SEQUENCE: 21

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Thr Ser Asn
            20                  25                  30

Ser Ile Ser Trp Val Arg Gln Ala Pro Gly Lys Gly Leu Glu Trp Val
        35                  40                  45

Ser Ala Ile Trp Ser Gly Gly Gly Thr Asp Tyr Asn Ser Asp Leu Lys
    50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Gly Tyr Pro Tyr Tyr Phe Asp Tyr Trp Gly Gln Gly Thr Leu
            100                 105                 110

Val Thr Val Ser Ser
        115

<210> SEQ ID NO 22
<211> LENGTH: 117
<212> TYPE: PRT
<213> ORGANISM: artificial
<220> FEATURE:
<223> OTHER INFORMATION: Heavy chain variable region of the humanized
    anti-CD11b antibodies-HC5

<400> SEQUENCE: 22

Glu Val Gln Leu Val Glu Thr Gly Gly Gly Leu Ile Gln Pro Gly Gly
1               5                   10                  15

Ser Leu Arg Leu Ser Cys Ala Ala Ser Gly Phe Ser Leu Thr Ser Asn
            20                  25                  30

Ser Ile Ser Trp Val Arg Gln Ala Pro Gly Lys Gly Leu Glu Trp Val
        35                  40                  45

Ser Ala Ile Trp Ser Gly Gly Gly Thr Asp Tyr Asn Ser Asp Leu Lys
    50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Gly Tyr Pro Tyr Tyr Phe Asp Tyr Trp Gly Gln Gly Thr Leu
            100                 105                 110

Val Thr Val Ser Ser
        115

<210> SEQ ID NO 23
<211> LENGTH: 108
<212> TYPE: PRT
<213> ORGANISM: artificial
<220> FEATURE:
<223> OTHER INFORMATION: Light chain variable region of the humanized
    anti-CD11b antibodies-VL1

<400> SEQUENCE: 23

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Asn Ile Gly Thr Ser

```
                    20                  25                  30

Ile His Trp Tyr Gln Gln Lys Pro Asp Gln Ser Pro Lys Leu Leu Ile
            35                  40                  45

Lys Tyr Ala Ser Glu Ser Ile Ser Gly Val Pro Ser Arg Phe Ser Gly
        50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Ser Asp Ser Trp Pro Thr
                85                  90                  95

Leu Thr Phe Gly Gln Gly Thr Lys Val Glu Ile Lys
            100                 105

<210> SEQ ID NO 24
<211> LENGTH: 108
<212> TYPE: PRT
<213> ORGANISM: artificial
<220> FEATURE:
<223> OTHER INFORMATION: Light chain variable region of the humanized
      anti-CD11b antibodies-VL2

<400> SEQUENCE: 24

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Asn Ile Gly Thr Ser
                20                  25                  30

Ile His Trp Tyr Gln Gln Lys Pro Gly Gln Ala Pro Arg Leu Leu Ile
            35                  40                  45

Tyr Tyr Ala Ser Glu Ser Ile Ser Gly Ile Pro Ala Arg Phe Ser Gly
        50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Ser Asp Ser Trp Pro Thr
                85                  90                  95

Leu Thr Phe Gly Gln Gly Thr Lys Leu Glu Ile Lys
            100                 105

<210> SEQ ID NO 25
<211> LENGTH: 108
<212> TYPE: PRT
<213> ORGANISM: artificial
<220> FEATURE:
<223> OTHER INFORMATION: Light chain variable region of the humanized
      anti-CD11b antibodies-VL3

<400> SEQUENCE: 25

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile Gly Thr Ser
                20                  25                  30

Ile His Trp Tyr Gln Gln Lys Pro Gly Lys Ala Pro Lys Leu Leu Ile
            35                  40                  45

Tyr Tyr Ala Ser Glu Ser Ile Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asp Ser Trp Pro Thr
                85                  90                  95

Leu Thr Phe Gly Gly Gly Thr Lys Val Glu Ile Lys
```

-continued

<210> SEQ ID NO 26
<211> LENGTH: 108
<212> TYPE: PRT
<213> ORGANISM: artificial
<220> FEATURE:
<223> OTHER INFORMATION: Light chain variable region of the humanized
      anti-CD11b antibodies-VL4

<400> SEQUENCE: 26

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Asn Ile Gly Thr Ser
            20                  25                  30

Ile His Trp Tyr Gln Gln Lys Pro Gly Gln Ala Pro Arg Leu Leu Ile
        35                  40                  45

Tyr Tyr Ala Ser Glu Ser Ile Ser Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Asp Ser Trp Pro Thr
                85                  90                  95

Leu Thr Phe Gly Gly Gly Thr Lys Val Glu Ile Lys
            100                 105

<210> SEQ ID NO 27
<211> LENGTH: 108
<212> TYPE: PRT
<213> ORGANISM: artificial
<220> FEATURE:
<223> OTHER INFORMATION: Light chain variable region of the humanized
      anti-CD11b antibodies-VL5

<400> SEQUENCE: 27

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Asn Ile Gly Thr Ser
            20                  25                  30

Ile His Trp Tyr Gln Gln Lys Pro Gly Gln Ala Pro Arg Leu Leu Ile
        35                  40                  45

Tyr Tyr Ala Ser Glu Ser Ile Ser Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Ser Asp Ser Trp Pro Thr
                85                  90                  95

Leu Thr Phe Gly Gln Gly Thr Lys Leu Glu Ile Lys
            100                 105

<210> SEQ ID NO 28
<211> LENGTH: 113
<212> TYPE: PRT
<213> ORGANISM: artificial
<220> FEATURE:
<223> OTHER INFORMATION: Light chain variable region of the humanized
      anti-CD11b antibodies-LC1

<400> SEQUENCE: 28

Asp Ile Val Met Thr Gln Ser Pro Asp Ser Leu Ala Val Ser Leu Gly
1               5                   10                  15

```
Glu Arg Ala Thr Ile Asn Cys Lys Ser Ser Gln Ser Leu Leu Tyr Ser
            20                  25                  30

Glu Asn Gln Glu Asn Tyr Leu Ala Trp Tyr Gln Gln Lys Pro Gly Gln
        35                  40                  45

Pro Pro Lys Leu Leu Ile Tyr Trp Ala Ser Thr Arg Gln Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                85                  90                  95

Tyr Tyr Asp Thr Pro Leu Thr Phe Gly Gln Gly Thr Lys Val Glu Ile
            100                 105                 110

Lys
```

<210> SEQ ID NO 29
<211> LENGTH: 113
<212> TYPE: PRT
<213> ORGANISM: artificial
<220> FEATURE:
<223> OTHER INFORMATION: Light chain variable region of the humanized
      anti-CD11b antibodies-LC2

<400> SEQUENCE: 29

```
Asp Ile Val Met Thr Gln Ser Pro Leu Ser Leu Pro Val Thr Pro Gly
 1               5                  10                  15

Glu Pro Ala Ser Ile Ser Cys Lys Ser Ser Gln Ser Leu Leu Tyr Ser
            20                  25                  30

Glu Asn Gln Glu Asn Tyr Leu Ala Trp Tyr Leu Gln Lys Pro Gly Gln
        35                  40                  45

Ser Pro Gln Leu Leu Ile Tyr Trp Ala Ser Thr Arg Gln Ser Gly Val
 50                  55                  60

Pro Asp Arg Phe Ser Gly Ser Gly Ser Gly Thr Asp Phe Thr Leu Lys
 65                  70                  75                  80

Ile Ser Arg Val Glu Ala Glu Asp Val Gly Val Tyr Tyr Cys Gln Gln
                85                  90                  95

Tyr Tyr Asp Thr Pro Leu Thr Phe Gly Gly Gly Thr Lys Val Glu Ile
            100                 105                 110

Lys
```

<210> SEQ ID NO 30
<211> LENGTH: 113
<212> TYPE: PRT
<213> ORGANISM: artificial
<220> FEATURE:
<223> OTHER INFORMATION: Light chain variable region of the humanized
      anti-CD11b antibodies-LC3

<400> SEQUENCE: 30

```
Asp Ile Val Met Thr Gln Ser Pro Leu Ser Leu Ser Val Thr Pro Gly
 1               5                  10                  15

Gln Pro Ala Ser Ile Ser Cys Lys Ser Ser Gln Ser Leu Leu Tyr Ser
            20                  25                  30

Glu Asn Gln Glu Asn Tyr Leu Ala Trp Tyr Leu Gln Lys Pro Gly Gln
        35                  40                  45

Ser Pro Gln Leu Leu Ile Tyr Trp Ala Ser Thr Arg Gln Ser Gly Val
 50                  55                  60

Pro Asp Arg Phe Ser Gly Ser Gly Ser Gly Thr Asp Phe Thr Leu Lys
```

```
                 65                  70                  75                  80
Ile Ser Arg Val Glu Ala Glu Asp Val Gly Val Tyr Tyr Cys Gln Gln
                 85                  90                  95

Tyr Tyr Asp Thr Pro Leu Thr Phe Gly Gln Gly Thr Lys Val Glu Ile
                100                 105                 110

Lys

<210> SEQ ID NO 31
<211> LENGTH: 113
<212> TYPE: PRT
<213> ORGANISM: artificial
<220> FEATURE:
<223> OTHER INFORMATION: Light chain variable region of the humanized
      anti-CD11b antibodies-LC4

<400> SEQUENCE: 31

Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Tyr Ser
                20                  25                  30

Glu Asn Gln Glu Asn Tyr Leu Ala Trp Phe Gln Gln Arg Pro Gly Gln
            35                  40                  45

Ser Pro Arg Arg Leu Ile Tyr Trp Ala Ser Thr Arg Gln Ser Gly Val
        50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Gln Gln
                85                  90                  95

Tyr Tyr Asp Thr Pro Leu Thr Phe Gly Gln Gly Thr Lys Leu Glu Ile
                100                 105                 110

Lys

<210> SEQ ID NO 32
<211> LENGTH: 113
<212> TYPE: PRT
<213> ORGANISM: artificial
<220> FEATURE:
<223> OTHER INFORMATION: Light chain variable region of the humanized
      anti-CD11b antibodies-LC5

<400> SEQUENCE: 32

Asp Ile Val Met Thr Gln Thr Pro Leu Ser Ser Pro Val Thr Leu Gly
1               5                   10                  15

Gln Pro Ala Ser Ile Ser Cys Lys Ser Ser Gln Ser Leu Leu Tyr Ser
                20                  25                  30

Glu Asn Gln Glu Asn Tyr Leu Ala Trp Leu Gln Gln Arg Pro Gly Gln
            35                  40                  45

Pro Pro Arg Leu Leu Ile Tyr Trp Ala Ser Thr Arg Gln Ser Gly Val
        50                  55                  60

Pro Asp Arg Phe Ser Gly Ser Gly Ala Gly Thr Asp Phe Thr Leu Lys
65                  70                  75                  80

Ile Ser Arg Val Glu Ala Glu Asp Val Gly Val Tyr Tyr Cys Gln Gln
                85                  90                  95

Tyr Tyr Asp Thr Pro Leu Thr Phe Gly Gln Gly Thr Lys Leu Glu Ile
                100                 105                 110

Lys
```